United States Patent
Jabbari

(10) Patent No.: US 12,208,168 B2
(45) Date of Patent: Jan. 28, 2025

(54) ENZYMATICALLY CLEAVABLE SELF-ASSEMBLED NANOPARTICLES FOR MORPHOGEN DELIVERY

(71) Applicant: UNIVERSITY OF SOUTH CAROLINA, Columbia, SC (US)

(72) Inventor: Esmaiel Jabbari, Bethesda, MD (US)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 0 days.

(21) Appl. No.: 18/308,810

(22) Filed: Apr. 28, 2023

(65) Prior Publication Data
US 2023/0355541 A1 Nov. 9, 2023

Related U.S. Application Data

(62) Division of application No. 16/811,023, filed on Mar. 6, 2020, now Pat. No. 11,672,767.

(60) Provisional application No. 62/847,024, filed on May 13, 2019.

(51) Int. Cl.
| A61K 38/00 | (2006.01) |
| A61K 9/51 | (2006.01) |
| A61K 47/65 | (2017.01) |
| C07K 7/00 | (2006.01) |
| A61K 38/18 | (2006.01) |

(52) U.S. Cl.
CPC .......... *A61K 9/5153* (2013.01); *A61K 9/5192* (2013.01); *A61K 47/65* (2017.08); *C07K 7/00* (2013.01); *A61K 38/1875* (2013.01)

(58) Field of Classification Search
CPC .... A61K 38/1875; A61K 47/62; A61K 47/65; A61K 47/6935; A61K 9/5153; A61K 9/5192; C07K 7/00
See application file for complete search history.

(56) References Cited

U.S. PATENT DOCUMENTS

| 5,037,883 | A | 8/1991 | Kopacek et al. |
| 6,342,221 | B1 | 1/2002 | Thorpe et al. |
| 6,346,349 | B1 | 2/2002 | Briscoe et al. |
| 6,348,209 | B2 | 2/2002 | Placke et al. |
| 6,884,432 | B2 | 4/2005 | Yaszemski et al. |
| 7,374,774 | B2 | 5/2008 | Bowlin et al. |
| 7,531,503 | B2 | 5/2009 | Atala et al. |
| 7,642,300 | B2 | 1/2010 | Yaszemski et al. |
| 7,737,131 | B2 | 6/2010 | Kiick et al. |
| 7,759,082 | B2 | 7/2010 | Bowlin et al. |
| 7,767,221 | B2 | 8/2010 | Lu et al. |
| 8,066,932 | B2 | 11/2011 | Xu |
| 8,071,722 | B2 | 12/2011 | Kaplan et al. |
| 8,202,551 | B2 | 6/2012 | Li et al. |
| 8,267,992 | B2 | 9/2012 | Atanasoska et al. |
| 8,449,622 | B2 | 5/2013 | McKay |
| 8,524,784 | B2 | 9/2013 | Sill et al. |
| 8,551,390 | B2 | 10/2013 | Jun et al. |
| 8,586,345 | B2 | 11/2013 | Simpson et al. |
| 8,691,543 | B2 | 4/2014 | Gaudette et al. |
| 9,101,654 | B2 | 8/2015 | Jabbari |
| 9,314,549 | B2 | 4/2016 | Jabbari |
| 9,808,555 | B2 | 11/2017 | Jabbari |
| 10,227,566 | B2 | 3/2019 | Jabbari |
| 2003/0215624 | A1 | 11/2003 | Layman et al. |
| 2004/0023028 | A1 | 2/2004 | Yaszemski et al. |
| 2004/0229333 | A1 | 11/2004 | Bowlin et al. |
| 2006/0067969 | A1 | 3/2006 | Lu et al. |
| 2006/0204441 | A1 | 9/2006 | Atala et al. |
| 2006/0204445 | A1 | 9/2006 | Atala et al. |
| 2006/0204539 | A1 | 9/2006 | Atala et al. |
| 2006/0241246 | A1 | 10/2006 | Yaszemski et al. |
| 2007/0018361 | A1 | 1/2007 | Xu |
| 2007/0043202 | A1 | 2/2007 | Yaszemski et al. |
| 2007/0269481 | A1 | 11/2007 | Li et al. |
| 2008/0038352 | A1 | 2/2008 | Simpson et al. |
| 2008/0065210 | A1 | 3/2008 | McKay |
| 2008/0102145 | A1 | 5/2008 | Kim et al. |
| 2008/0109070 | A1 | 5/2008 | Wagner et al. |
| 2008/0159985 | A1 | 7/2008 | Bowlin et al. |
| 2008/0206308 | A1 | 8/2008 | Jabbari et al. |

(Continued)

FOREIGN PATENT DOCUMENTS

| WO | WO 2005/004811 | 1/2005 |
| WO | WO 2005/020849 | 3/2005 |

OTHER PUBLICATIONS

Castelletto et al. (Langmuir 2010, 26(12), 9986-9996). Self-Assembly of PEGylated Peptide Conjugates Containing a Modified Amyloid ß-Peptide Fragment. (Year: 2010).*

(Continued)

*Primary Examiner* — Aradhana Sasan
*Assistant Examiner* — Mercy H Sabila
(74) *Attorney, Agent, or Firm* — DORITY & MANNING, P.A.

(57) ABSTRACT

The present disclosure is directed to hybrid multifunctional macromers that can self-assemble to form nanoparticles for on-demand and targeted release of morphogens. Embodiments of the disclosure can include the hybrid multifunctional macromers and peptide sequences incorporated therein, self-assembled nanoparticles including the hybrid multifunctional macromers, methods for producing the hybrid multifunctional macromers and peptide sequences, and methods for treating a disease by the on-demand and targeted delivery of a compound using the hybrid multifunctional macromers.

18 Claims, 23 Drawing Sheets
Specification includes a Sequence Listing.

(56) References Cited

U.S. PATENT DOCUMENTS

| | | |
|---|---|---|
| 2008/0213389 A1 | 9/2008 | Lelkes et al. |
| 2008/0220042 A1 | 9/2008 | Hashi et al. |
| 2008/0220054 A1 | 9/2008 | Shastri et al. |
| 2009/0110732 A1 | 4/2009 | Jabbari |
| 2010/0047309 A1 | 2/2010 | Lu et al. |
| 2010/0084784 A1 | 4/2010 | Jabbari |
| 2010/0086607 A1 | 4/2010 | Jabbari |
| 2010/0322979 A1 | 12/2010 | Jabbari |
| 2010/0327494 A1 | 12/2010 | Jabbari |
| 2011/0142950 A1* | 6/2011 | Sill ............... A61K 9/1075 514/459 |
| 2012/0226295 A1 | 9/2012 | Jabbari |
| 2013/0338791 A1 | 12/2013 | McCullen et al. |
| 2014/0349367 A1 | 11/2014 | Jabbari |
| 2014/0350692 A1 | 11/2014 | Jabbari |
| 2015/0175972 A1 | 6/2015 | Jabbari |
| 2016/0250379 A1 | 9/2016 | Jabbari |

OTHER PUBLICATIONS

Toledano et al. (J. Am. Chem. Soc. 2006, 128, 4, 1070-1071). Enzyme-Triggered Self-Assembly of Peptide Hydrogels via Reversed Hydrolysis. J. Am. Chem. Soc. 2006, 128, 1070-1071 (Year: 2006).*
Galler et al. (J. Am. Chem. Soc. 2010, 132, 3217-3223). Self-assembling Multidomain Peptide Hydrogels: Designed Susceptibility to Enzymatic Cleavage Allows Enhanced Cell Migration and Spreading. J. Am. Chem. Soc. 2010, 132, 3217-3223. (Year: 2010).*
Castelletto et al. (European Polymer Journal 49 (2013) 2961-2967). Self-assembly and bioactivity of a polymer/peptide conjugate containing the RGD cell adhesion motif and PEG. (Year: 2013).*
Adam, et al. "Signaling through PI3K/AKT mediates stretch and PDGF-BB-dependent DNA synthesis in bladder smooth muscle cells" *J Urol.* 169 (2003) pp. 2388-2393.
Adler-Abramovich, et al. "Thermal and Chemical Stability of Diphenylalanine Peptide Nanotubes: Implications for Nanotechnological Applications" *Langmuir* 22 (2006) pp. 1313-1320.
Amini, et al. "Bone tissue engineering: recent advances and challenges" *Crit. Rev™ Biomed. Eng.* 40 (2012) pp. 363-408.
Anderson, et al. "Post-Traumatic Osteoarthritis: Improved Understanding and Opportunities for Early Intervention" *J. Orthop. Res.* 29(6) (2011) pp. 802-809.
Andrades, et al. "Induction of superficial zone protein (SZP)/lubricin/PRG 4 in muscle-derived mesenchymal stem/progenitor cells by transforming growth factor-β1 and bone morphogenetic protein-7" *Arthritis Res. Ther.* 14(2):R72 (2012) pp. 1-7.
Annabi, et al. "Rational Design and Applications of Hydrogels in Regenerative Medicine" *Adv. Mater.* 26 (2014) pp. 85-124.
Aoyama, et al. "Keratin Nanofiber Scaffold for Vascular Graft" *Tissue Eng. Part A* 21 (2015) p. S244.
Arai, et al. "Tie2/Angiopoietin-1 Signaling Regulates Hematopoietic Stem Cell Quiescence in the Bone Marrow Niche" *Cell* 118 (2004) pp. 149-161.
Arai, et al. "Amino acid sequence of feather keratin from fowl" *Eur. J. Biochem.* 132 (1983) pp. 506-507.
Audouin, et al. "Surface-initiated RAFT polymerization of NIPAM from monolithic macroporous polyHIPE" *Eur. Polymer J.* 49(5) (2013) pp. 1073-1079.
Backes, et al. "Synthesis of positional scanning libraries of fluorogenic peptide substrates to define the extended substrate specificity of plasmin and thrombin" *Nat. Biotechn.* 18 (2000) pp. 187-193.
Badve, et al. "Breast-cancer stem cells-beyond semantics" *Lancet Oncol.* 13 (2012) pp. e43-e48.
Balaji, et al. "The role of mesenchymal stem cells in the regenerative wound healing phenotype" *Adv. Wound Care* 1 (2012) pp. 159-165.
Balaji, et al. "Characterization of keratin-collagen 3D scaffold for biomedical applications" *Polym. Adv. Tech.* 23 (2012) pp. 500-507.
Barati, et al. "Synthesis and characterization of photo-cross-linkable keratin hydrogels for stem cell Encapsulation" *Biomacromol.* 18(2) (2017) pp. 398-412.
Barati, et al. "Spatiotemporal release of BMP-2 and VEGF enhances osteogenic and vasculogenic differentiation of human mesenchymal stem cells and endothelial colony-forming cells co-encapsulated in a patterned hydrogel" *J. Contr. Rel.* 223 (2016) pp. 126-136.
Barati, et al. "Effect of Organic Acids on Calcium Phosphate Nucleation and Osteogenic Differentiation of Human Mesenchymal Stem Cells on Peptide Functionalized Nanofibers" *Langmuir* 31 (2015) pp. 5130-5140.
Barati, et al. "Time dependence of material properties of polyethylene glycol hydrogels chain extended with short hydroxy acid segments" *Polymer* 55 (2014) pp. 3894-3904.
Barone, et al. "Thermally processed keratin films" *J. Appl. Poly. Sci.* 97 (2005) pp. 1644-1651.
Bernardes, et al. "Facile conversion of cysteine and alkyl cysteines to dehydroalanine on protein surfaces: versatile and switchable access to functionalized proteins" *J. Am. Chem. Soc.* 130 (2008) pp. 5052-5053.
Bhardwaj, et al. "Silk fibroin-keratin based 3D scaffolds as a dermal substitute for skin tissue engineering" *Integ. Biol.* 7 (2015) pp. 53-63.
Bhat-Nakshatri, et al. "SLUG/SNAI2 and tumor necrosis factor generate breast cancer cells with CD44+/CD24-phenotype" *BMC Cancer* 10:411 (2010) pp. 1-16.
Biddle, et al. "Cancer stem cells and EMT in carcinoma" *Cancer Metastasis Rev.* 31 (2012) pp. 285-293.
Britton, et al. "Breast cancer, side population cells and ABCG2 expression" *Cancer Lett.* 323 (2012) pp. 97-105.
Bryant, et al. "Hydrogel properties influence ECM production by chondrocytes photoencapsulated in poly(ethylene glycol) hydrogels" *J. Biomed. Mater. Res.* 59 (2002) pp. 63-72.
Burdick, et al. "Photoencapsulation of osteoblasts in injectable RGD-modified PEG hydrogels for bone tissue engineering" *Biomater.* 23 (2002) pp. 4315-4323.
Burnett, et al. "Hemostatic properties and the role of cell receptor recognition in human hair keratin protein hydrogels" *Biomaterials* 34 (2013) pp. 2632-2640.
Buxton, et al. "Design and Characterization of Poly(Ethylene Glycol) Photopolymerizable Semi-Interpenetrating Networks for Chondrogenesis of Human Mesenchymal Stem Cells" *Tissue Eng.* 13 (2007) pp. 2549-2560.
Carragee, et al. "A critical review of recombinant human bone morphogenetic protein-2 trials in spinal surgery: emerging safety concerns and lessons learned" *Spine J.* 11 (2011) pp. 471-491.
Castano, et al. "The tumor macroenvironment and systemic regulation of breast cancer progression" *Intl. J. Dev. Biol.* 55 (2011) pp. 889-897.
Castelletto, et al. "Self-assembly of PEGylated peptide conjugates containing a modified amyloid β-peptide fragment" *Langmuir* 26 (2010) pp. 9986-9996.
Chalker, et al. "Chemical modification of proteins at cysteine: Opportunities in chemistry and biology" *Chemistry* 4 (2009) pp. 630-640.
Chan, et al. "Crosslinking of collagen scaffolds promotes blood and lymphatic vascular stability" *J. Biomed. Mater. Res. Part A* 102 (2014) pp. 3186-3195.
Chen, et al. "A Universal and Facile Approach for the Formation of a Protein Hydrogel for 3D Cell Encapsulation" *Adv. Funct. Mater.* 25 (2015) pp. 6189-6198.
Chen, et al. "Engineering Vascularized Tissue Constructs using an Injectable Cell-laden Collagen Hydrogel" *Tissue Eng. Part A* 21 (2015) p. S102.
Chen, et al. "Geometric Control of Cell Life and Death" *Science* 276 (1997) pp. 1425-1428.
Chirila, et al. "Poly(2-hydroxyethyl methacrylate) sponges as implant materials: In vivo and in vitro evaluation of cellular invasion" *Biomaterials* 14(1) (1993) pp. 26-38.
Cushing, et al. "Hydrogel Cell Cultures" *Science* 316 (2007) pp. 1133-1135.
Damodaran, et al. "Protein PEGylation: An overview of chemistry and process considerations" *Eur. Pharm. Rev.* 15 (2010) pp. 18-26.
Dawson, et al. "Biomaterials for stem cell differentiation" *Adv. Drug Deliv. Rev.* 60 (2008) pp. 215-228.

(56) References Cited

OTHER PUBLICATIONS

D'Este, et al. "Evaluation of an injectable thermoresponsive hyaluronan hydrogel in a rabbit osteochondral defect model" *J. Biomed. Mater. Res. Part A* 104(6) (2016) pp. 1469-1478.
Debnath, et al. "Modelling Glandular Epithelial Cancers in Three-Dimensional Cultures" *Nature Rev. Cancer* 5 (2005) pp. 675-688.
Del Vecchio, et al. "Epidermal growth factor receptor variant III contributes to cancer stem cell phenotypes in invasive breast carcinoma" *Cancer Res.* 72(10) (2012) pp. 2657-2671.
Desale, et al. "Biodegradable hybrid polymer micelles for combination drug therapy in ovarian cancer" *J. Contr. Rel.* 171 (2013) pp. 339-348.
Discher, et al. "Tissue Cells Feel and Respond to the Stiffness of Their Substrate" *Science* 310 (2005) pp. 1139-1143.
Dong, et al. "In Situ 'Clickable' Zwitterionic Starch-Based Hydrogel for 3D Cell Encapsulation" *Appl. Mater. Interf.* 8 (2016) pp. 4442-4455.
Dong, et al. "Injectable Hybrid Hydrogel for Mesenchymal Stem Cell Delivery, from PEG-based Multifunctional Hyperbranched Polymers" *Tissue Eng. Part A* 21 (2015) pp. S298-S299.
Doroski, et al. "Cyclic Tensile Culture Promotes Fibroblastic Differentiation of Marrow Stromal Cells Encapsulated in Poly(Ethylene Glycol)-Based Hydrogels" *Tissue Eng. Part A* 16 (2010) pp. 3457-3466.
Eastoe, J.E. "The amino acid composition of mammalian collagen and gelatin" *Biochem. J.* 61 (1955) pp. 589-600.
Elisseeff, et al. "Photoencapsulation of chondrocytes in poly(ethylene oxide)-based semi-interpenetrating networks" *J. Biomed. Mater. Res.* 51 (2000) pp. 164-171.
Engler, et al. "Embryonic cardiomyocytes beat best on a matrix with heart-like elasticity: Scar-like rigidity inhibits beating" *J. Cell Sci.* 121 (2008) pp. 3794-3802.
Engler, et al. "Extracellular matrix elasticity directs stem cell differentiation" *J. Musculosk. Neuron. Inter.* 7(4) (2007) p. 335.
Engler, et al. "Matrix Elasticity Directs Stem Cell Lineage Specification" *Cell* 126 (2006) pp. 677-689.
Evans, et al. "Use of Genetically Modified Muscle and Fat Grafts to Repair Defects in Bone and Cartilage" *Eur. Cells Mater.* 18 (2009) pp. 96-111.
Falah, et al. "Treatment of articular cartilage lesions of the knee" *Intl. Ortho.* 34(5) (2010) pp. 621-630.
Ferlin, et al. "Development of a Dynamic Stem Cell Culture Platform for Mesenchymal Stem Cell Adhesion and Evaluation" *Molecul. Pharma.* 11 (2014) pp. 2172-2181.
Fernandez-Gonzalez, et al. "Ch. 1: In situ analysis of cell populations: Long-term label-retaining cells" *Meth. Molecul. Biol.: Protocols for Adult Stem Cells* 621 (2010) pp. 1-28.
Fillmore, et al. "Human breast cancer cell lines contain stem-like cells that self-renew, give rise to phenotypically diverse progeny and survive chemotherapy" *Breast Cancer Res.* 10:R25 (2008) pp. 1-13.
Flanagan, et al. "Neurite branching on deformable substrates" *Neuroreport* 13 (2002) pp. 2411-2415.
Floor, et al. "Cancer cells in epithelial-to-mesenchymal transition and tumor-propagating-cancer stem cells: Distinct, overlapping or same populations" *Oncogene* 30 (2011) pp. 4609-4621.
Fraser, et al. "Keratins: Their composition, structure, and biosynthesis" *Charles C. Thomas* (1972) pp. 1-304.
Fu, et al. "3D cell entrapment in crosslinked thiolated gelatin-poly(ethylene glycol) diacrylate hydrogels" *Biomater.* 33 (2012) pp. 48-58.
Fuhrmann, et al. "Injectable hydrogel promotes early survival of induced pluripotent stem cell-derived oligodendrocytes and attenuates longterm teratoma formation in a spinal cord injury model" *Biomaterials* 83 (2016) pp. 23-36.
Fukumoto, et al. "Combined effects of insulin-like growth factor-1 and transforming growth factor-β1 on periosteal mesenchymal cells during chondrogenesis in vitro" *Osteoarth. Cart.* 11(1) (2003) pp. 55-64.

Galler et al. Self-assembling Multidomain Peptide Hydrogels: Designed Susceptibility to Enzymatic Cleavage Allows Enhanced Cell Migration and Spreading. J. Am. Chem. Soc. 2010, 132, (2010), pp. 3217-3223.
Ghajar, et al. "Mesenchymal cells stimulate capillary morphogenesis via distinct proteolytic mechanisms" *Exp. Cell Res.* 316 (2010) pp. 813-825.
Ghajar, et al. "Mesenchymal stem cells enhance angiogenesis in mechanically viable prevascularized tissues via early matrix metalloproteinase upregulation" *Tiss. Eng.* 12 (2006) pp. 2875-2888.
Gill, et al. "The association of mammographic density with ductal carcinoma in situ of the breast: The Multiethnic Cohort" *Breast Cancer Res.* 8:R30 (2006) pp. 1-6.
Golub, et al. "The Role of Alkaline Phosphatase in Cartilage Mineralization" *Bone and Mineral* 17 (1992) pp. 273-278. (Abstract only).
Gorman, J. "Materials Take Wing: What to do with 4 billion pounds of feathers?" *Science News* 161 (2002) pp. 120-121.
Grange, et al. "SCA-1 identifies the tumor-initiating cells in mammary tumors of BALB-neuT transgenic mice" *Neoplasia* 10 (2008) pp. 1433-1443.
Grogan, et al. "Zone-Specific Gene Expression Patterns in Articular Cartilage" *Arthr. Rheum.* 65(2) (2013) pp. 418-428.
Guo, et al. "Triphenylalanine peptides self-assemble into nanospheres and nanorods that are different from the nanovesicles and nanotubes formed by diphenylalanine peptides" *Nanoscale* 6 (2014) pp. 2800-2811.
Guo, et al. "In vitro generation of an osteochondral construct using injectable hydrogel composites encapsulating rabbit marrow mesenchymal stem cells" *Biomaterials* 30 (2009) pp. 2741-2752.
Gupta, et al. "Identification of selective inhibitors of cancer stem cells by high-throughput screening" *Cell* 138 (2009) pp. 645-659.
Habel, et al. "Mammographic density and breast cancer after ductal carcinoma in situ" *J. Natl. Cancer Inst.* 96 (2004) pp. 1467-1472.
Hacker et al. Multi-Functional Macromers for Hydrogel Design in Biomedical Engineering and Regenerative Medicine. Int. J. Mol. Sci. 2015, 16,(2015), pp. 27677-27706.
Han, et al. "Alkylation of human hair keratin for tunable hydrogel erosion and drug delivery in tissue engineering applications" *Acta Biomater.* 23 (2015) pp. 201-213.
Han, et al. "Bioerodable PLGA-Based Microparticles for Producing Sustained-Release Drug Formulations and Strategies for Improving Drug Loading" *Front. Pharmacol.* 7:185 (2016) pp. 1-11.
Haralson, et al. "Extracellular matrix: A practical approach" *Annales de Biologie Clinique* 10(54) (1996) pp. 383-384.
Harris, et al. "Rapid and general profiling of protease specificity by using combinatorial fluorogenic substrate libraries" *PNAS* 97 (2000) pp. 7754-7759.
Haycock, J.W. "Ch. 1: 3D cell-culture: A review of current approaches and techniques" *Meth. Mol. Biol.: 3D Cell Culture: Methods and Protocols* 695 (2011) pp. 1-15.
He, et al. "Combined effect of osteopontin and BMP-2 derived peptides grafted to an adhesive hydrogel on osteogenic and vasculogenic differentiation of marrow stromal cells" *Langmuir* 28 (2012) pp. 5387-5397.
He, et al. "Effect of grafting RGD and BMP-2 protein-derived peptides to a hydrogel substrate on osteogenic differentiation of marrow stromal cells" *Langmuir* 24 (2008) pp. 12508-12516.
He, et al. "Material properties and cytocompatibility of injectable MMP degradable poly(lactide ethylene oxide fumarate) hydro gel as a carrier for marrow stromal cells" *Biomacromolecules* 8 (2007) pp. 780-792.
He, et al. "Cellular and Molecular Regulation of hematopoietic and Intestinal Stem Cell Behavior" *Ann. N.Y. Acad. Sci.* 1049 (2005) pp. 28-38.
Heddleston, et al. "Hypoxia inducible factors in cancer stem cells" *Br. J. Cancer* 102 (2010) pp. 789-795.
Henderson, et al. "Concurrent differentiation of marrow stromal cells to osteogenic and vasculogenic lineages" *Macromol. Biosci.* 8 (2008) pp. 499-507.
Hoffman, A.S. "Hydrogels for biomedical applications" *Adv. Drug Deliv. Rev.* 64 (2012) pp. 18-23.

(56) References Cited

OTHER PUBLICATIONS

Hsu, et al. "A family business: Stem cell progeny join the niche to regulate homeostasis" *Nat. Rev. Mol. Cell Biol.* 13 (2012) pp. 103-114.

Huang, et al. "The role of substrate topography on the cellular uptake of nanoparticles" *J. Biomed. Mater. Res. Pt. B* 104 (2016) pp. 488-495.

Huebsch, et al. "Harnessing traction-mediated manipulation of the cell/matrix interface to control stem-cell fate" *Nat. Mater.* 9 (2010) pp. 518-526.

James, et al. "A Review of the Clinical Side Effects of Bone Morphogenetic Protein-2" *Tiss. Eng. Pt. B Rev.* 22 (2016) pp. 284-297.

Jayathilakan, et al. "Utilization of byproducts and waste materials from meat, poultry and fish processing industries: A review" *J. Food Sci. Techn.* 49 (2012) pp. 278-293.

Kachgal, et al. "Mesenchymal stem cells from adipose and bone marrow promote angiogenesis via distinct cytokine and protease expression mechanisms" *Angiogenesis* 14 (2011) pp. 47-59.

Kai, et al. "Breast cancer stem cells" *Breast Cancer* 17 (2010) pp. 80-85.

Kakkar, et al. "Extraction and characterization of keratin from bovine hoof: A potential material for biomedical applications" *SpringerPlus* 3:596 (2014) pp. 1-9.

Karaman, et al. "Effect of surface modification of nanofibres with glutamic acid peptide on calcium phosphate nucleation and osteogenic differentiation of marrow stromal cells" *J. Tiss. Eng. Regen. Med.* 10 (2016) pp. E132-E146.

Karimi, et al. "A developmentally inspired combined mechanical and biochemical signaling approach on zonal lineage commitment of mesenchymal stem cells in articular cartilage regeneration" *Integr. Biol.* 7 (2015) pp. 112-127.

Katoh, M. "Networking of WNT, FGF, NOTCH, BMP, and Hedgehog signaling pathways during carcinogenesis" *Stem Cell Rev.* 3 (2007) pp. 30-38.

Kazemzadeh-Narbat, et al. "Engineering Photocrosslinkable Bicomponent Hydrogel Constructs for Creating 3D Vascularized Bone" *Adv. Healthc. Mater.* 6:1601122 (2017) pp. 1-11.

Kelly, et al. "How to study proteins by circular dichroism" *Biochimica et Biophysica Acta* 1751 (2005) pp. 119-139.

Kempen, et al. "Effect of local sequential VEGF and BMP-2 delivery on ectopic and orthotopic bone regeneration" *Biomater.* 30 (2009) pp. 2816-2825.

Keung, et al. "Presentation Counts: Microenvironmental Regulation of Stem Cells by Biophysical and Material Cues" *Ann. Rev. Cell Dev. Biol.* 26 (2010) pp. 533-556.

Kim, et al. "OCT4 Expression Enhances Features of Cancer Stem Cells in a Mouse Model of Breast Cancer" *Lab. Anim. Res.* 27(2) (2011) pp. 147-152.

Klein, et al. "Depth-dependent biomechanical and biochemical properties of fetal, newborn, and tissue-engineered articular cartilage" *J. Biomech.* 40(1) (2007) pp. 182-190.

Korkaya, et al. "Breast cancer stem cells, cytokine networks, and the tumor microenvironment" *J. Clin. Inv.* 121(10) (2011) pp. 3804-3809.

Krohn, et al. "CXCR4 receptor positive spheroid forming cells are responsible for tumor invasion in vitro" *Cancer Lett.* 280 (2009) pp. 65-71.

Kwon, et al. "In vivo osteogenic differentiation of human turbinate mesenchymal stem cells in an injectable in situ-forming hydrogel" *Biomaterials* 35 (2014) pp. 5337-5346.

Lam, et al. "Osteochondral defect repair using bilayered hydrogels encapsulating both chondrogenically and osteogenically pre-differentiated mesenchymal stem cells in a rabbit model" *Osteoarth. Cart.* 22(9) (2014) pp. 1291-1300.

Leal-Egaña, et al. "Determination of pore size distribution at the cell-hydrogel interface" *J. Nanobiotechn.* 9:24 (2011) pp. 1-7.

Lee, et al. "Mesenchymal stem cells and cutaneous wound healing: novel methods to increase cell delivery and therapeutic efficacy" *Stem Cell Res. Ther.* 7:37 (2016) pp. 1-8.

Lee, et al. "Gel microstructure regulates proliferation and differentiation of MC3T3-E1 cells encapsulated in alginate beads" *Acta Biomaterialia* 8 (2012) pp. 1693-1702.

Lee, et al. "Regeneration of the articular surface of the rabbit synovial joint by cell homing: A proof of concept study" *Lancet* 376 (2010) pp. 440-448.

Lee, et al. "Protein-resistant surfaces prepared by PEO-containing block copolymer surfactants" *J. Biomed. Mater. Res.* 23 (1989) pp. 351-368.

Levental, et al. "Matrix crosslinking forces tumor progression by enhancing integrin signaling" *Cell* 139 (2009) pp. 891-906.

Li, et al. "The Effect of Oxygen Tension on Human Articular Chondrocyte Matrix Synthesis: Integration of Experimental and Computational Approaches" *Biotechn. Bioeng.* 111(9) (2014) pp. 1876-1885.

Li, et al. "Normal Stem Cells and Cancer Stem Cells: The Niche Matters" *Cancer Res.* 66(9) (2006) pp. 4553-4557.

Liang, et al. "A cell-instructive hydrogel to regulate malignancy of 3D tumor spheroids with matrix rigidity" *Biomaterials* 32 (2011) pp. 9308-9315.

Lin, et al. "Allyl sulfides are privileged substrates in aqueous cross-metathesis: application to site-selective protein modification" *J. Am. Chem. Soc.* 130 (2008) pp. 9642-9643.

Liu, et al. "Identification of tumorsphere- and tumor-initiating cells in HER2/Neu-induced mammary tumors" *Cancer Res.* 67 (2007) pp. 8671-8681.

Liu, et al. "Biomimetic hydrogels for chondrogenic differentiation of human mesenchymal stem cells to neocartilage" *Biomaterials* 31 (2010) pp. 7298-7307.

Livak, et al. "Analysis of relative gene expression data using real-time quantitative PCR and the $2^{-\Delta\Delta C_T}$ Method" *Methods* 25 (2001) pp. 402-408.

Long, et al. "Improving the mechanical properties of collagen-based membranes using silk fibroin for corneal tissue engineering" *J. Biomed. Mater. Res. Part A* 103 (2015) pp. 1159-1168.

Lotz, M.K. "Posttraumatic osteoarthritis: Pathogenesis and pharmacological treatment options" *Arthr. Res. Ther.* 12(3):211 (2010) pp. 1-9.

LV, et al. "Structural and functional evaluation of oxygenating keratin/silk fibroin scaffold and initial assessment of their potential for urethral tissue engineering" *Biomaterials* 84 (2016) pp. 99-110.

Ma, et al. "Enhanced biological stability of collagen porous scaffolds by using amino acids as novel cross-linking bridges" *Biomaterials* 25 (2004) pp. 2997-3004.

Mabry, et al. "Microarray analyses to quantify advantages of 2D and 3D hydrogel culture systems in maintaining the native valvular interstitial cell phenotype" *Biomaterials* 74 (2016) pp. 31-41.

Mahato, R.I. "Biomaterials for delivery and targeting of proteins and nucleic acids" *CRC* Press (2004) pp. 1-679.

Mak, et al. "Indian hedgehog signals independently of PTHrP to promote chondrocyte hypertrophy" *Development* 135(11) (2008) pp. 1947-1956.

Mandal, et al. "Self-assembly of peptides to nanostructures" *Org. Biomolec. Chem.* 12 (2014) pp. 3544-3561.

Mariani, et al. "Signaling Pathways in Cartilage Repair" *Intl. J. Molecul. Sci.* 15(5) (2014) pp. 8667-8698.

Masters, et al. "Designing scaffolds for valvular interstitial cells: Cell adhesion and function on naturally derived materials" *J. Biomed. Mater. Res. Part A* 71 (2004) pp. 172-180.

Matson, et al. "Self-assembling peptide scaffolds for regenerative medicine" *Chem. Comm.* 48 (2012) pp. 26-33.

Melrose, et al. "Chondroitin sulphate and heparan sulphate sulphation motifs and their proteoglycans are involved in articular cartilage formation during human foetal knee joint development" *Histochem. Cell Biol.* 138(3) (2012) pp. 461-475.

Mercado, et al. "Effect of grafting BMP2-derived peptide to nanoparticles on osteogenic and vasculogenic expression of stromal cells" *J. Tissue Eng. Regen. Med.* 8(1) (2014) pp. 15-28.

Mercado, et al. "Effect of encapsulation or grafting on release kinetics of recombinant human bone morphogenetic protein-2 from self-assembled poly (lactide-co-glycolide ethylene oxide fumarate) nanoparticles" *Microsc. Res. Tech.* 73 (2010) pp. 824-833.

(56) References Cited

OTHER PUBLICATIONS

Mi, et al. "Adverse effects of adenovirus-mediated gene transfer of human transforming growth factor β1 into rabbit knees" *Arthritis Res. Ther.* 5(3) (2003) pp. R132-R139.

Mironi-Harpaz, et al. "Photopolymerization of cell-encapsulating hydrogels: Crosslinking efficiency versus cytotoxicity" *Acta Biomaterialia* 8 (2012) pp. 1838-1848.

Moeinzadeh, et al. "Comparative effect of physicomechanical and biomolecular cues on zone-specific chondrogenic differentiation of mesenchymal stem cells" *Biomaterials* 92 (2016) pp. 57-70.

Moeinzadeh, et al. "Experimental and computational investigation of the effect of hydrophobicity on aggregation and osteoinductive potential of BMP-2-derived peptide in a hydrogel matrix" *Tiss. Eng. Pt. A* 21 (2015) pp. 134-146.

Moeinzadeh, et al. "Nanostructure Formation and Transition from Surface to Bulk Degradation in Polyethylene Glycol Gels Chain-Extended with Short Hydroxy Acid Segments" *Biomacromol.* 14 (2013) pp. 2917-2928.

Moeinzadeh, et al. "Gelation Characteristics and Osteogenic Differentiation of Stromal Cells in Inert Hydrolytically Degradable Micellar Polyethylene Glycol Hydrogels" *Biomacromolecules* 13 (2012) pp. 2073-2086.

Moeinzadeh, et al. "Mesoscale simulation of the effect of a lactide segment on the nanostructure of star poly(ethylene glycol-co-lactide)-acrylate macromonomers in aqueous solution" *J. Phys. Chem. B* 116 (2012) pp. 1536-1543.

Moeinzadeh, et al. "Synthesis and gelation characteristics of photo-crosslinkable star poly(ethylene oxide-co-lactide-glycolide acrylate) macromonomers" *Polymer* 52 (2011) pp. 3887-3896.

Monteiro, et al. "Nanoparticle-based bioactive agent release systems for bone and cartilage tissue engineering" *Reg. Ther.* 1 (2015) pp. 109-118.

Munoz-Pinto, et al. "Collagen-mimetic hydrogels promote human endothelial cell adhesion, migration and phenotypic maturation" *J. Mater. Chem. B* 3 (2015) pp. 7912-7919.

Mura, et al. "Stimuli-responsive nanocarriers for drug delivery" *Nat. Mater.* 12 (2013) pp. 991-1003.

Namba, et al. "Spontaneous repair of superficial defects in articular cartilage in a fetal lamb model" *J. Bone Joint Surg.* 80A(1) (1998) pp. 4-10.

Nemir, et al. "Synthetic Materials in the Study of Cell Response to Substrate Rigidity" *Ann. Biomed. Eng. Soc.* (2009) 38(1) pp. 2-20.

Neuss, et al. "Secretion of fibrinolytic enzymes facilitates human mesenchymal stem cell invasion into fibrin clots" *Cells Tiss. Org.* 191 (2010) pp. 36-46.

Nichol, et al. "Cell-laden microengineered gelatin methacrylate hydrogels" *Biomaterials* 31 (2010) pp. 5536-5544.

Oliveira, et al. "The osteogenic differentiation of rat bone marrow stromal cells cultured with dexamethasone-loaded carboxymethylchitosan/poly(amidoamine) dendrimer nanoparticles" *Biomater.* 30 (2009) pp. 804-813.

Oliver-Welsh, et al. "Deciding how best to treat cartilage defects" *Orthopedics* 39 (2016) pp. 343-350.

Orth, et al. "Reliability, Reproducibility, and Validation of Five Major Histological Scoring Systems for Experimental Articular Cartilage Repair in the Rabbit Model" *Tissue Eng. Part C Meth.* 18(5) (2012) pp. 329-339.

Pace, et al. "A Human Hair Keratin Hydrogel Scaffold Enhances Median Nerve Regeneration in Nonhuman Primates: An Electrophysiological and Histological Study" *Tissue Eng. Part A* 20 (2014) pp. 507-517.

Pampaloni, et al. "The third dimension bridges the gap between cell culture and live tissue" *Nature Rev. Molec. Cell Biol.* 8 (2007) pp. 839-845.

Pan, et al. "Self-assembled supramolecular systems for bone engineering applications" *Curr. Opin. Coll. Interf. Sci.* 35 (2018) pp. 104-111.

Panda, et al. "Short peptide based self-assembled nanostructures: implications in drug delivery and tissue engineering" *Polym. Chem.* 5 (2014) pp. 4418-4436.

Papadopoulos, et al. "Injectable and photopolymerizable Tissue-Engineered Auricular Cartilage Using Poly(Ethylene Glycol) Dimethacrylate Copolymer Hydrogels" *Tissue Eng. Part A* 17 (2011) pp. 161-169.

Parekh, et al. "Modulus-driven differentiation of marrow stromal cells in 3D scaffolds that is independent of myosin-based cytoskeletal tension" *Biomaterials* 32 (2011) pp. 2256-2264.

Pascher, et al. "Gene delivery to cartilage defects using coagulated bone marrow aspirate" *Gene Ther.* 11(2) (2004) pp. 133-141.

Paszek, et al. "Tensional homeostasis and the malignant phenotype" *Cancer Cell* 8 (2005) pp. 241-254.

Patel et al. "Biodegradable polymer scaffold for tissue engineering" *Trends Biomater. Artif. Organs* 25 (2011) pp. 20-29.

Pek, et al. "The effect of matrix stiffness on mesenchymal stem cell differentiation in a 3D thixotropic gel" *Biomaterials* 31 (2010) pp. 385-391.

Peng, et al. "Long-term sphere culture cannot maintain a high ratio of cancer stem cells: A mathematical model and experiment" *PLoS One* 6(11):e25518 (2011) pp. 1-6.

Peppas, et al. "Characterization of the crosslinked structure of hydrogels" *Hydrogel Med. Pharm.: vol. 1 Fund.* CRC Press, Inc. (1986) pp. 27-56.

Petersen, et al. "Interaction with basement membrane serves to rapidly distinguish growth and differentiation pattern of normal and malignant human breast epithelial cells" *Proc. Natl. Acad. Sci. USA* 89 (1992) pp. 9064-9068.

Pfaff, K. "A third of soldiers disabled after ACI for lesions in the knee" *Orthop. Today* (2014) pp. 1-2.

Pfaffl, M.W. "A new mathematical model for relative quantification in real-time RT-PCR" *Nucl. Acids Res.* 29 (2001) pp. 2002-2007.

Provenzano, et al. "Matrix density-induced mechanoregulation of breast cell phenotype, signaling and gene expression through a FAK-ERK linkage" *Oncogene* 28 (2009) pp. 4326-4343.

Punzi, et al. "Post-traumatic arthritis: Overview on pathogenic mechanisms and role of inflammation" *Rheum. Musculosk. Dis.* 2(2):e000279 (2016) pp. 1-9.

Raof, et al. "Bioengineering embryonic stem cell microenvironments for exploring inhibitory effects on metastatic breast cancer cells" *Biomaterials* 32 (2011) pp. 4130-4139.

Reches, et al. "Formation of Closed-Cage Nanostructures by Self-Assembly of Aromatic Dipeptides" *Nano Lett.* 4 (2004) pp. 581-585.

Rehfeldt, et al. "Cell responses to the mechanochemical microenvironment—Implications for regenerative medicine and drug delivery" *Adv. Drug Deliv. Rev.* 59 (2007) pp. 1329-1339.

Rehmann, et al. "Tuning microenvironment modulus and biochemical composition promotes human mesenchymal stem cell tenogenic differentiation" *J. Biomed. Mater. Res. Part A* 104 (2016) pp. 1162-1174.

Rhim, et al. "EMT and dissemination precede pancreatic tumor formation" *Cell* 148 (2012) pp. 349-361.

Ries, et al. "MMP-2, MT1-MMP, and TIMP-2 are essential for the invasive capacity of human mesenchymal stem cells: differential regulation by inflammatory cytokines" *Blood* 109 (2007) pp. 4055-4063.

Rivera, et al. "Post-traumatic OA: Unique implications for the military" *Lower Extr. Rev.* (2013) pp. 43-46.

Rivera, et al. "Posttraumatic osteoarthritis caused by battlefield injuries: The primary source of disability in warriors" *J. Am. Acad. Orthop. Surg.* 20(1) (2012) pp. S64-S69.

Rouse, et al. "A Review of Keratin-Based Biomaterials for Biomedical Applications" *Materials* 3 (2010) pp. 999-1014.

Samani, et al. "Elastic moduli of normal and pathological human breast tissues: An inversion-technique-based investigation of 169 samples" *Phys. Med. Biol.* 52 (2007) pp. 1565-1576.

Saravanan, et al. "Exploration on the Amino Acid Content and Morphological Structure in Chicken Feather Fiber" *J. Text. Appar. Techn. Man.* 7(3) (2012) pp. 1-6.

Sawada, et al. "Scaffold for Cell Culture Made by Electrospun Keratin Nanofibers" *Tissue Eng. Part A* 20 (2014) p. S65.

(56) References Cited

OTHER PUBLICATIONS

Sawhney, et al. "Interfacial photopolymerization of poly(ethylene glycol)-based hydrogels upon alginate-poly (l-lysine) microcapsules for enhanced biocompatibility" *Biomaterials* 14(13) (1993) pp. 1008-1016.
Schefe, et al. "Quantitative real-time RT-PCR data analysis: current concepts and the novel 'gene expression's CT difference' formula" *J. Mol. Med.* 84 (2006) pp. 901-910.
Schmitt, et al. "Long-Segment Fusion for Adult Spinal Deformity Correction Using Low-Dose Recombinant Human Bone Morphogenetic Protein-2: A Retrospective Review of Fusion Rates" *Neurosurgery* 79 (2016) pp. 212-221.
Schrader, et al. "Matrix Stiffness Modulates Proliferation, Chemotherapeutic Response, and Dormancy in Hepatocellular Carcinoma Cells" *Hepatology* 53(4) (2011) pp. 1192-1205.
Shaw, et al. "Introduction to polymer viscoelasticity" *John Wiley & Sons, Inc.* (2005) pp. 1-372.
Silverstein, et al. "Spectrometric identification of organic compounds" *John Wiley & Sons, Inc.* (1991) pp. 1-550.
Simank, et al. "Effects of local application of growth and differentiation factor-5 (GDF-5) in a full-thickness cartilage defect model" *Growth Factors* 22(1) (2004) pp. 35-43.
Singer, et al. "Cutaneous wound healing" *New Eng. J. Med.* 341 (1999) pp. 738-746.
Singhvi, et al. "Engineering cell shape and function" *Science* 264 (1994) pp. 696-698.
Smith, et al. "Three-Dimensional Culture of Mouse Renal Carcinoma Cells in Agarose Macrobeads Selects for a Subpopulation of Cells with Cancer Stem Cell or Cancer Progenitor Properties" *Cancer Res.* 71(3) (2011) pp. 716-724.
Soeda, et al. "Hypoxia promotes expansion of the CD133-positive glioma stem cells through activation of HIF-1α" *Oncogene* 28 (2009) pp. 3949-3959.
Song, et al. "Amphiphilic Peptide Nanorods Based on Oligo-Phenylalanine as a Biocompatible Drug Carrier" *Bioconj. Chem.* 28 (2017) pp. 2266-2276.
Stenman, et al. "Trypsin-2 degrades human type II collagen and is expressed and activated in mesenchymally transformed rheumatoid arthritis synovitis tissue" *Am. J. Path.* 167 (2005) pp. 1119-1124.
Stockwell, R.A. "Interrelationship of Cell Density and Cartilage Thickness in Mammalian Articular Cartilage" *J. Anat.* 109 (1971) pp. 411-421.
Studer, et al. "Molecular and Biophysical Mechanisms Regulating Hypertrophic Differentiation in Chondrocytes and Mesenchymal Stem Cells" *Eur. Cells Mater.* 24 (2012) pp. 118-135.
Suk, et al. "PEGylation as a strategy for improving nanoparticle-based drug and gene delivery" *Adv. Drug Deliv. Rev.* 99 (2016) pp. 28-51.
Sun, et al. "Forcing Stem Cells to Behave: A Biophysical Perspective of the Cellular Microenvironment" *Annu. Rev. Biophys.* 41 (2012) pp. 519-542.
Tan, et al. "Fabrication and Evaluation of Porous Keratin/Chitosan (KCS) Scaffolds for Effectively Accelerating Wound Healing" *Biomed. Enviro. Sci.* 28 (2015) pp. 178-189.
Tanabe, et al. "Fabrication and characterization of chemically crosslinked keratin films" *Mater. Sci. Eng.: C* 24 (2004) pp. 441-446.
Tao, et al. "Imagable 4T1 model for the study of late stage breast cancer" *BMC Cancer* 8:228 (2008) pp. 1-19.
Tilghman, et al. "Matrix Rigidity Regulates Cancer Cell Growth and Cellular Phenotype" *PLoS One* 5(9):e12905 (2010) pp. 1-13.
Toledano et al. Enzyme-Triggered Self-Assembly of Peptide Hydrogels via Reversed Hydrolysis. J. Am. Chem. Soc. 2006, 128, (2006), pp. 1070-1071.
Tropel, et al. "Isolation and characterization of mesenchymal stem cells from adult mouse bone marrow" *Exper. Cell Res.* 295 (2004) pp. 395-406.
Tschumperlin, et al. "Mechanotransduction through growth-factor shedding into the extracellular space" *Nature* 429 (2004) pp. 83-86.

Tzokova, et al. "The effect of PEO length on the self-assembly of poly(ethylene oxide)-tetrapeptide conjugates prepared by "Click" chemistry" *Langmuir* 25 (2009) pp. 11082-11089.
Van Rijt, et al. "Enhancing regenerative approaches with nanoparticles" *J. Royal Soc. Interf.* 14:20170093 (2017) pp. 1-10.
Vargo-Gogola, et al. "Modelling breast cancer: One size does not fit all" *Nat. Rev. Cancer* 7 (2007) pp. 659-672.
Verbridge, et al. "Tissue-engineered three-dimensional tumor models to study tumor angiogenesis" *Tissue Eng. Part A* 16 (2010) pp. 2147-2152.
Verma, et al. "Preparation of scaffolds from human hair proteins for tissue-engineering applications" *Biomed. Mater.* 3(2):025007 (2008) pp. 1-12.
Verschure, et al. "Localization of insulin-like growth factor-1 receptor in human normal and osteoarthritic cartilage in relation to proteoglycan synthesis and content" *Br. J. Rheumatol.* 35(11) (1996) pp. 1044-1055.
Vincent, et al. "Basic fibroblast growth factor mediates transduction of mechanical signals when articular cartilage is loaded" *Arthr. Rheum.* 50 (2004) pp. 526-533.
Visser, et al. "Crosslinkable Hydrogels Derived from Cartilage, Meniscus, and Tendon Tissue" *Tissue Eng. Part A* 21(7-8) (2015) pp. 1195-1206.
Wagegg, et al. "Hypoxia Promotes Osteogenesis but Suppresses Adipogenesis of Human Mesenchymal Stromal Cells in a Hypoxia-Inducible Factor-1 Dependent Manner" *PloS One* 7(9):e46483 (2012) pp. 1-11.
Walker, N.G. "The role of mesenchymal stem cells from adult human bone marrow in in vitro wound models" *U. Sheffield* (2013) pp. 1-226.
Wang, et al. "Human keratin hydrogels support fibroblast attachment and proliferation in vitro" *Cell Tissue Res.* 347 (2012) pp. 795-802.
Wang, et al. "TGFβ signaling in cartilage development and maintenance" *Birth Def. Res. Part C: Embryo Today Rev.* 102(1) (2014) pp. 37-51.
Watson, et al. "Gene delivery of TGF-β1 induces arthrofibrosis and chondrometaplasia of synovium in vivo" *Lab. Invest.* 90(11) (2010) pp. 1615-1627.
Wehling, et al. "Interleukin-1β and Tumor Necrosis Factor α Inhibit Chondrogenesis by 16 Human Mesenchymal Stem Cells Through NF-κ B-Dependent Pathways" *Arthr. Rheum.* 60(3) (2009) pp. 801-812.
Weiswald, et al. "In situ protein expression in tumour spheres: Development of an immunostaining protocol for confocal microscopy" *BMC Cancer* 10:106 (2010) pp. 1-11.
Welm, et al. "Isolation and characterization of functional mammary gland stem cells" *Cell Prolif.* 36(Suppl. 1) (2003) pp. 17-32.
Williamson, et al. "Growth of immature articular cartilage in vitro: Correlated variation in tensile biomechanical and collagen network properties" *Tissue Eng.* 9(4) (2003) pp. 625-634.
Wong, et al. "Chondrocyte biosynthesis correlates with local tissue strain in statically compressed adult articular cartilage" *J. Orthop. Res.* 15(2) (1997) pp. 189-196.
Woodward, et al. "On mammary stem cells" *J. Cell Sci.* 118 (2005) pp. 3585-3594.
Wu, et al. "Human developmental chondrogenesis as a basis for engineering chondrocytes from pluripotent stem cells" *Stem Cell Rep.* 1(6) (2013) pp. 575-589.
Xu, et al. "Water-Stable Three-Dimensional Ultrafine Fibrous Scaffolds from Keratin for Cartilage Tissue Engineering" *Langmuir* 30 (2014) pp. 8461-8470.
Yamauchi, et al. "Preparation of stable aqueous solution of keratins, and physiochemical and biodegradational properties of films" *J. Biomed. Mater. Res.* 31 (1996) pp. 439-444.
Yang, et al. "Effect of CD44 Binding Peptide Conjugated to an Engineered Inert Matrix on Maintenance of Breast Cancer Stem Cells and Tumorsphere Formation" *PLoS One* 8(3):e59147 (2013) pp. 1-15.
Yang, et al. "Three-Dimensional-Engineered Matrix to Study Cancer Stem Cells and Tumorsphere Formation: Effect of Matrix Modulus" *Tissue Eng. Part A* 19(5-6) (2013) pp. 669-685.

(56) References Cited

OTHER PUBLICATIONS

Yang, et al. "Engineering Orthopedic Tissue Interfaces" *Tissue Eng. Part B Rev.* 15(2) (2009) pp. 127-141.
Yin, et al. "Study on effective extraction of chicken feather keratins and their films for controlling drug release" *Biomater. Sci.* 1 (2013) pp. 528-536.
Yip, et al. "A multicellular 3D heterospheroid model of liver tumor and stromal cells in collagen gel for anti-cancer drug testing" *Biochem. Biophys. Res. Comm.* 433 (2013) pp. 327-332.
Yu, et al. "Kruppel-like factor 4 (KLF4) is required for maintenance of breast cancer stem cells and for cell migration and invasion" *Oncogene* 30 (2011) pp. 2161-2172.
Yue, et al. "Synthesis, properties, and biomedical applications of gelatin methacryloyl (GelMA) hydrogels" *Biomaterials* 73 (2015) pp. 254-271.
Zaman, et al. "Migration of tumor cells in 3D matrices is governed by matrix stiffness along with cell-matrix adhesion and proteolysis" *Proc. Natl. Acad. Sci. USA* 103(29) (2006) pp. 10889-10894.
Zeisberg, et al. "Biomarkers for epithelial-mesenchymal transitions" *J. Clin. Invest.* 119 (2009) pp. 1429-1437.
Zhang, et al. "VEGF and BMP-2 Promote Bone Regeneration by Facilitating Bone Marrow Stem Cell Homing and Differentiation" *Eur. Cells Mater.* 27 (2014) pp. 1-12.
Zhang, et al. "The role of tissue engineering in articular cartilage repair and regeneration" *Crit. Rev. Biomed. Eng.* 37(1-2) (2009) pp. 1-57.
Zisch, et al. "Cell-demanded release of growth factors" *Comp Biomater.* vol. 4 (2011) pp. 463-473.

\* cited by examiner

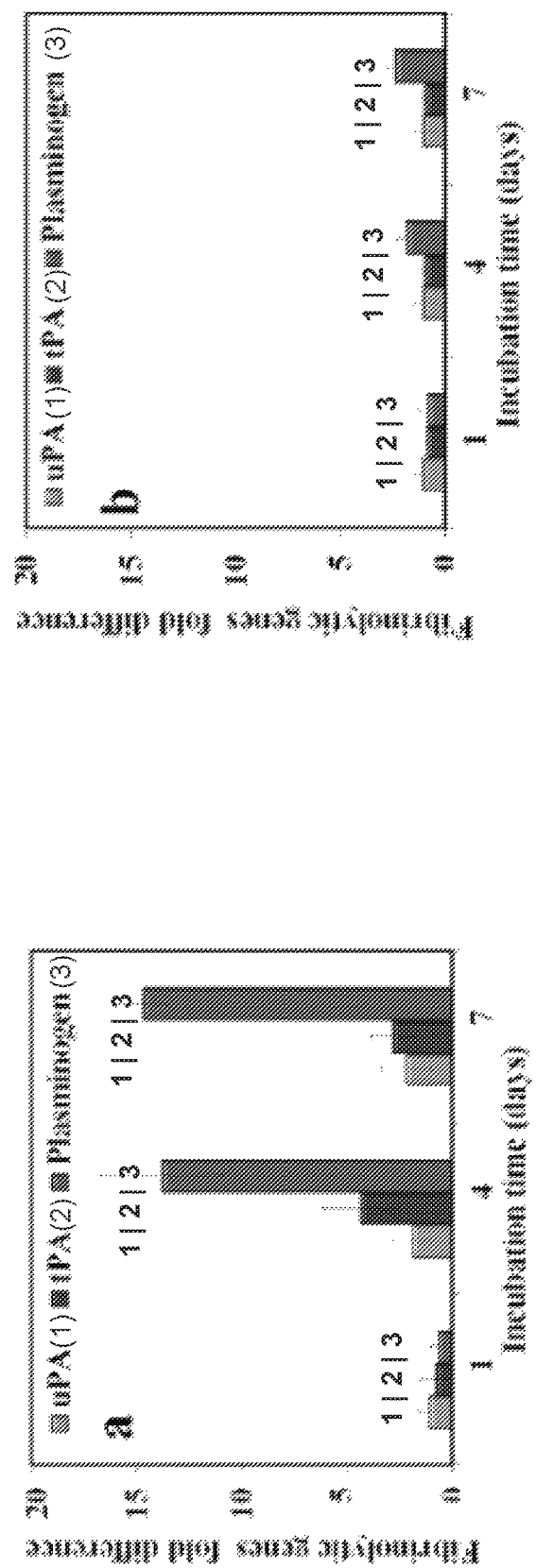
FIG. 3B
FIG. 3A
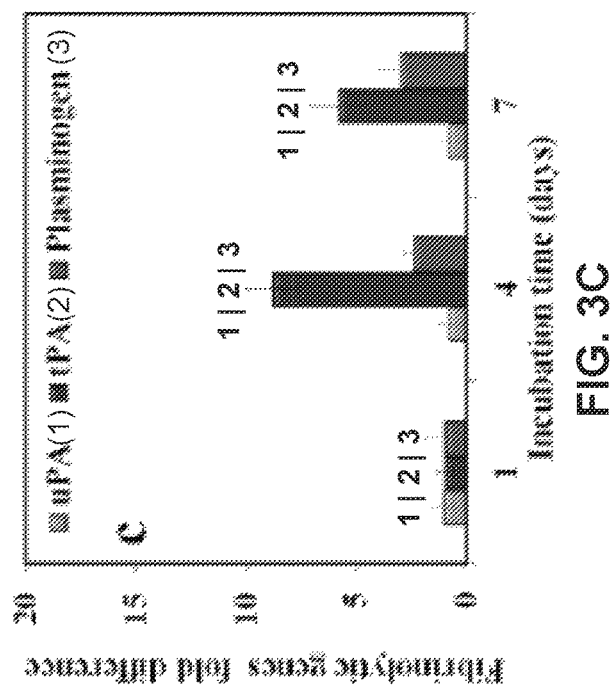
FIG. 3C

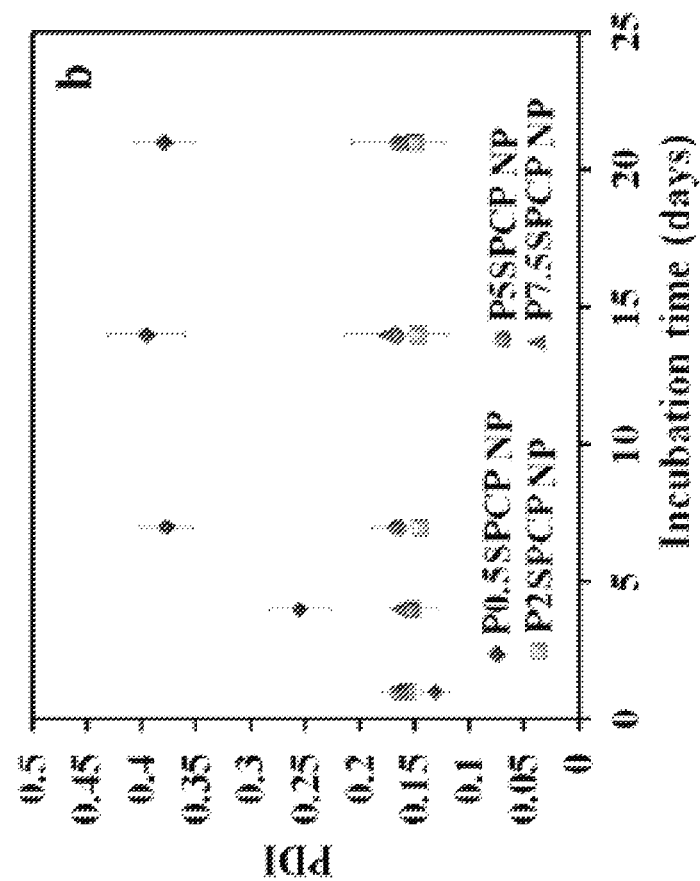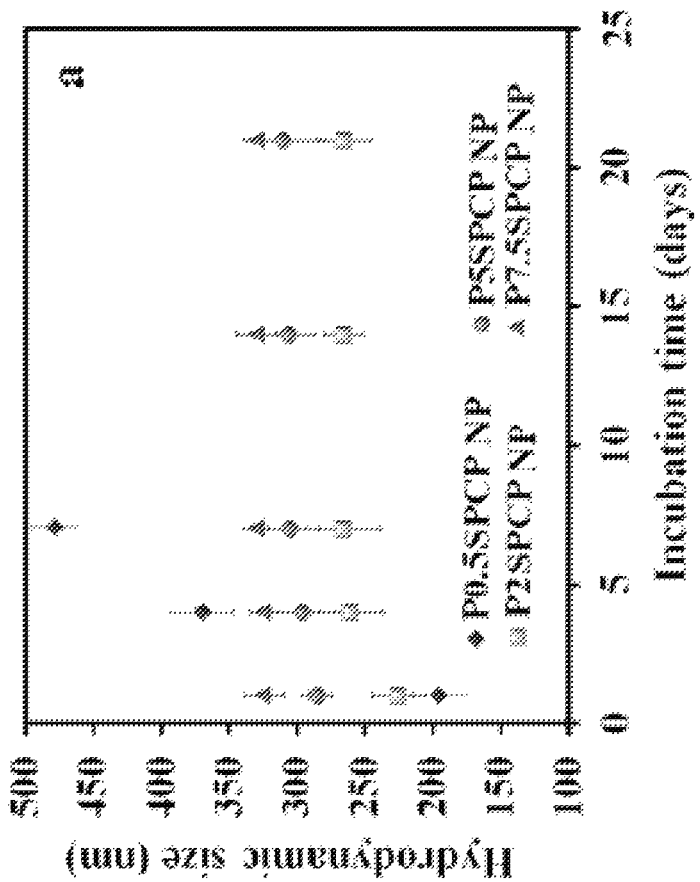
FIG. 6B
FIG. 6A

ENZYMATICALLY CLEAVABLE SELF-ASSEMBLED NANOPARTICLES FOR MORPHOGEN DELIVERY

CROSS REFERENCE TO RELATED APPLICATIONS

This application is a divisional application of U.S. patent application Ser. No. 16/811,023, filed on Mar. 6, 2020, which claims filing benefit of U.S. Provisional Patent Application Ser. No. 62/847,024, filed on May 13, 2019, all of which are incorporated herein by reference.

STATEMENT AS TO RIGHTS TO INVENTIONS MADE UNDER FEDERALLY SPONSORED RESEARCH

This invention was made with Government support under Contract Nos. 1403545 and 1500242, awarded by the National Science Foundation (NSF), and Contract No. R56 AR063745, awarded by the National Institute of Arthritis and Musculoskeletal and Skin Diseases of the National institutes of Health (NIH). The Government has certain rights in the invention.

SEQUENCE LISTING

This application contains a Sequence Listing which has been submitted electronically in XML format and is hereby incorporated by reference in its entirety. Said XML copy, created on Jul. 14, 2023, is named USC-622-DIV_1350_SL.xml and is 24,902 bytes in size.

BACKGROUND

There is a continuing need to develop approaches for controlled release of morphogens in applications such as tissue regeneration. While metal and ceramic particles have been used as delivery systems, these materials can have drawbacks because even though they are biocompatible, there is risk for accumulation in the body, something that may be a particular issue when the site of delivery is already damaged by an injury. Needed in the art are alternative delivery systems that can be functionalized in various ways to both target and trigger release of a compound without leading to bioaccumulation.

In particular, enzyme responsive delivery systems have yet to be developed that take advantage of the secretion of enzymes such as proteases by mesenchymal stem cells (MSCs) and endothelial colony forming cells (ECFCs). Both of these cells express proteases to degrade the extracellular matrix (ECM) as they migrate to sites of injury. MSCs invade the ECM during angiogenesis via different protease families including the plasmin axis of serine proteases and the plasmin-independent matrix metalloproteinases (MMPs). Human MSCs have a strong fibrinolytic activity by expressing key elements of the fibrinolytic cascade including urokinase plasminogen activator (uPA) and its receptor (uPAR), tissue plasminogen activator (tPA) and plasminogen inhibitor PAI. Further, it has been shown that the expression level of fibrinolytic enzymes tPA and uPA in hMSCs is dependent on factors that mediate vascularization and bone formation like basic fibroblast growth factor (bFGF), transforming growth factor-$\beta$ (TGF-$\beta$) and interleukin-10 (IL-1$\beta$). Studies on fibrinolytic capacity of MSCs in a fibrin clot indicate that the activity of plasmin and the extent of fibrin degradation during wound healing is controlled by MSCs. By developing nanoparticles that can target and trigger release of a compound at sites of injury without bioaccumulation, difficult applications in tissue engineering can by addressed such as the reconstruction of skeletal defects.

SUMMARY OF THE INVENTION

The present disclosure is directed to hybrid multifunctional macromers that can self-assemble to form nanoparticles for on-demand and targeted release of morphogens. Embodiments of the disclosure can include the hybrid multifunctional macromers and peptide sequences incorporated therein, self-assembled nanoparticles including the hybrid multifunctional macromers, methods for producing the hybrid multifunctional macromers and peptide sequences, and methods for treating a disease by the on-demand and targeted delivery of a compound using the hybrid multifunctional macromers.

Embodiments of the disclosure can provide improved biocompatibility compared to inorganic delivery vehicles while demonstrating therapeutically efficacious treatments for applications such as promoting vascularized osteogenesis. Other features and aspects of the present invention are set forth in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

FIGS. 3A-3F illustrate bar graphs comparing different conditions in accordance with exemplary embodiments of the disclosure.

FIGS. 6A-6D illustrate graphs displaying characteristics (respectively: hydrodynamic size, PDI, ellipticity, and cell viability) of nanoparticles formed in accordance with the disclosure.

Figure 1:
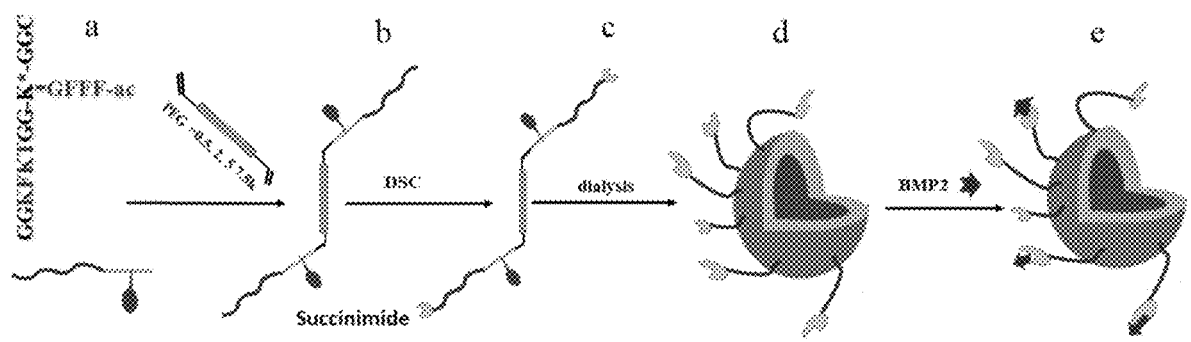
FIG. 1 illustrates an example process for forming a nanoparticle from a hybrid multifunctional macromer in accordance with exemplary embodiments of the disclosure and 1 illustrates SEQ ID NO: 17.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only and is not intended as limiting the broader aspects of the present invention, which broader aspects are embodied exemplary constructions.

Generally speaking, the present invention is directed to hybrid multifunctional macromers that can self-assemble to form nanoparticles for on-demand and targeted release of morphogens. Embodiments of the disclosure can include the hybrid multifunctional macromers and peptide sequences incorporated therein, self-assembled nanoparticles including the hybrid multifunctional macromers and peptide sequences, methods for producing hybrid multifunctional macromers and peptide sequences, and methods for treating a disease by the on-demand and targeted delivery of a compound.

An example embodiment of the disclosure can include a hybrid multifunctional macromer. The hybrid multifunctional macromer formed in accordance with the disclosure includes a cleavage site, an assembly site, and a solubility region. In general, the cleavage site includes a first amino acid sequence that can be cleaved by a protein; the assembly site includes a second amino acid sequence that can organize through a non-covalent interaction (e.g., pi-pi stacking) to produce a higher order structure; and the solubility region includes a water-soluble polymer. Each of the cleavage site, the assembly site, and the solubility region are linked to one another by one or more covalent bonds to form an exemplary hybrid multifunctional macromer.

In some embodiments, the hybrid multifunctional macromer can include more than one cleavage site. For these embodiments, each cleavage site can have the same or different first amino acid sequences. As an example implementation, the first amino acid sequence can include lysine-phenylalanine-tyrosine-lysine (KFYK (SEQ ID NO: 2)), which can be cleaved by plasmin to break one or more of the bonds linking the residues of the first amino acid sequence. As another example implementation, the first amino acid sequence can include the sequence QPQGLAK (SEQ ID NO: 3) that is cleaved by MMP-13 enzyme. Though not intended to limit the scope of first amino acid sequences that can be included in the cleavage site, any MMP-/plasmin-cleavable sequence as known in the art can be included in the first amino acid sequence.

In some embodiments, the hybrid multifunctional macromer can include more than one assembly site. For these embodiments, each assembly site can have the same or different second amino acid sequences. As an example implementation, the second amino acid sequence can include at least one phenylalanine (F), such as 2-8 phenylalanine residues (F . . . F). Additionally, in certain implementations, the phenylalanine residues can be sequentially linked such that each phenylalanine is directly linked to the next phenylalanine (e.g., FFF, FFFF (SEQ ID NO: 4), and FFFFFFFF (SEQ ID NO: 5)) without any other amino acids or linkers between each phenylalanine residue. As another example implementation, the second amino acid sequence can include the sequence VVVVVVKK (SEQ ID NO: 6) that assembles into vesicles or other sequences that naturally assemble into nanostructures.

Another aspect of the cleavage site, the assembly site, or both sites include a residue number describing the number of amino acid residues present in the site. For example, the residue number for the amino acid sequence KFYK (SEQ ID NO: 2) is 4 since it includes 4 amino acids. As another example, the residue number for the amino acid sequence FFF is 3. Thus, an example hybrid multifunctional macromer in accordance with the disclosure can include at least one cleavage site having a first amino acid sequence that includes at least 4 amino acids. The at least 4 amino acids can include any of combination of the 20 canonical amino acids that can be cleaved by a protein.

In some embodiments, the hybrid multifunctional macromer can include more than one solubility region. For these embodiments, each solubility region can include the same or different water-soluble polymer. As an example implementation, the water-soluble polymer can include polyethylene glycol (PEG). An aspect of polymers is the ability to adjust the molecular weight of the polymer by altering the degree of polymerization. In some embodiments, the water-soluble polymer can include PEG having a molecular weight between about 1.5 kDa to about 5 kDa; for example, about 1.3 kDa to about 7 kDa or about 1.2 kDa to about 9 kDa. As another example implementation, the water-soluble polymer can include poly(vinyl alcohol) (PVA), copolymers of PEG and PVA, polyvinylpyrrolidone (PVP), copolymers of PEG and PVP, copolymers of PVA and PVP, or terpolymers of PEG, PVA and PVP, or other water-soluble polymers as known in the art.

In embodiments of the disclosure, the hybrid multifunctional macromer can further include one or more linkers. For these embodiments, the linkers may be used to covalently link the cleavage site, the assembly site, and/or the solubility region to one another. For example, an embodiment of the disclosure can include a hybrid multifunctional macromer having a linker (e.g., succinimide) covalently linking an amino acid residue from the cleavage site to the solubility region. As another example embodiment, a hybrid multifunctional macromer of the disclosure can include at least two linkers to covalently link an amino acid residue from a first cleavage site to the solubility region, and to covalently link an amino acid residue from a second cleavage site to the solubility region. In an example implementation, the amino acid residue from the cleavage site can include a cysteine which, upon reaction with maleimide, forms a covalent bond by addition to the thiol group to maleimide ring double bond producing a succinimide linker.

As an example implementation, the linker can include succinimide. In some implementations, the succinimide can be functionalized at the nitrogen (N) bridge to include a hydroxyl (—OH) or propanamide (—CH$_2$CH$_2$CONH$_2$) substitution.

In some embodiments, the hybrid multifunctional macromer can also include an endcap. In an example implementation, the endcap may include a molecule, protein, or other compound linked to the C-terminus and/or N-terminus of an oligopeptide sequence included in the hybrid multifunctional macromer. The endcap can also include a modification such as C-terminus amidation, N-terminus acetylation, or addition of a protecting group.

For embodiments of the disclosure, the hybrid multifunctional macromer can include a sequence order which defines, in part, the connectivity between one or more of the cleavage site, the assembly site, and the solubility region. An aspect of the sequence order can include one or more regions. Each region can include a cleavage site, an assembly site, and/or a solubility region. For hybrid multifunctional macromers that include more than one region, such that both regions include a cleavage site, an assembly site, or a solubility region, the regions are not constrained to require the same cleavage site, assembly site, or solubility region. Example hybrid multifunctional macromers according to the disclosure may include two regions, each region including a cleavage site and an assembly site. In some implementations, the assembly site for each region can be the same (e.g., FFF). In certain implementations, the assembly site for each region can be different (e.g., the first region includes FFF and the second region includes FFFFFFFF (SEQ ID NO: 5).

Additionally, or alternatively, to define the amino acid sequences in each region, the sequence order can be used to define connectivity between regions. For example, a hybrid multifunctional macromer can include a first region including a cleavage site and an assembly site, a second region including a solubility region, and a third region including a cleavage site and an assembly site. The connectivity may include the first region covalently linked to the second region and the second region covalently linked to the third region. In some implementations, regions can be linked at either the C-terminus or N-terminus, which is referred to as backbone-linked since these regions are attached by the backbone of the multifunctional macromer. In certain implementations, the different regions can be linked by a side group of a peptide included in the region. Generally, linkage of one region to a second region does not require that the regions are backbone-linked, and any amino acid, monomer, or linker in the region may be used to form a covalent bond.

Another aspect of the hybrid multifunctional macromer disclosed herein can include a backbone sequence, the backbone sequence including a linear sequence of amino acids which contains the cleavage site. In some implementations, the backbone sequence can include a number of amino acid residues between 6 to 24, such as 8-18, or 9-14. Further, in some embodiments, the multifunctional peptide sequence can include the assembly site linked to a side group of a residue in the backbone sequence, rather than linked to the N-terminus or C-terminus. As an example, the assembly site may be linked to a side chain of an amino acid residue (e.g., lysine, aspartic acid, and glutamic acid). By linking the assembly site to a side chain in the backbone sequence, certain embodiments can include non-linear hybrid multifunctional macromers where the assembly site is not linked to the macromer backbone.

For embodiments having the assembly site linked to a side group of a residue, the assembly site can include a terminus modification. For example, extending a peptide chain from the nitrogen of lysine can result in a free amino group that may be modified (e.g., acetylated) to prevent ionization. As another example, extending a peptide chain from the carboxylate of aspartic acid can result in a free carboxylate group that may be modified (e.g., amidated) to prevent ionization. Thus, in some example embodiments, the assembly site can include a terminus modification such as an N-acetylated residue or a C-amidated residue.

An example embodiment of the disclosure can also include a method for forming a hybrid multifunctional peptide sequence, the method including: synthesizing a backbone amino acid sequence by linking 4-26 amino acids, the backbone amino acid sequence comprising a cleavage site; synthesizing an assembly peptide by linking an assembly site to an amino acid side chain included in the hybrid multifunctional backbone sequence; and attaching a solubility region to the hybrid multifunctional macromer. Generally, for embodiments of the disclosure, the order of synthesis does not matter, and each of the cleavage site, the assembly site, and the solubility region may be linked to one another in any order.

In some implementations, synthesizing the backbone amino acid sequence may be conducted chemically (e.g., by solid phase synthesis) to chemically attach the residues in the backbone sequences. In certain implementations, the backbone amino acid sequence or a substantial portion of the backbone amino acid sequence may be produced using an organism by providing a vector encoding the amino acid sequence to the organism.

In an example embodiment, the method for forming a hybrid multifunctional macromer can include synthesizing a backbone amino acid sequence by linking 12 amino acids to form the sequence GGKFYKGGKGGC (SEQ. ID No: 1) which comprises the cleavage site KFYK (SEQ ID NO: 2). An assembly site can be linked to the backbone amino acid sequence by attaching one or more phenylalanine residues to a lysine in the example sequence. For instance, the $9^{th}$ residue (K9) of SEQ. ID No: 1 can be linked to an assembly site containing at least one phenylalanine (e.g., GFFF (SEQ ID NO: 7)) to form an assembly peptide. To produce the example hybrid multifunctional macromer, a solubility region can be attached to the multifunctional sequence already containing the cleavage site and an assembly site. In an example implementation, the solubility region can be attached to the multifunctional sequence by linking the solubility region to a residue of the backbone sequence. For instance, the $12^{th}$ residue (C12) of SEQ. ID No: 1 can be linked to the solubility region.

In some example methods for forming a hybrid multifunctional macromer as disclosed herein, the methods may also include attaching a linker, a spacer, or an endcap to the backbone sequence or the assembly site.

An embodiment of the disclosure can also include a method for delivering a compound (e.g., a protein such as bone morphogenic protein or BMP) to a patient in need thereof by administering a nanoparticle composed substantially from hybrid multifunctional macromer as disclosed herein. In general, the nanoparticle composed substantially from the hybrid multifunctional macromer, can include mainly the hybrid multifunctional macromer (e.g., 99% or greater purity by weight). While solvents or ions may be associated with the nanoparticles, these do not affect the purity of the nanoparticles. In an example implementation, the nanoparticle can include a group (e.g., greater than 1) of hybrid multifunctional macromers, where at least one macromer includes an endcap containing the compound. Upon cleavage by a protein, a portion of the macromer including the compound can be released to provide targeted delivery of the compound.

In an embodiment of the disclosure, the method for delivering a compound to a patient can include using an administration route. For example, the administration route can include one or more of the following: intravenous injection, intramuscular injection, oral capsule, sublingual tablet, skin ointment, or anal suppository.

EXAMPLE 1

Example 1 discusses various methods and procedures and provides exemplary embodiments that may be understood in conjunction with the Drawings and Description provided herein. The specific methods and procedures described in Example 1 are not meant to limit the disclosure and are provided solely to illustrate some of the ways in which the invention may be practiced.

Methods

Materials: Actide (L) monomer with >99.5% purity (Ortec, Easley, SC) was dried. PEG with molecular weights (MW) of 2.0, 5.0 and 7.5 kDa, PEGDA with 575 Da MW, porcine skin gelatin (type A, 300 bloom), tin (II) 2-ethylhexanoate (TOC), dimethyl sulfoxide (DMSO), methacrylic anhydride (MA), Alizarin red, and 4,6 diamidino-2-phenylindole (DAPI) were received from Sigma-Aldrich (St. Louis, MO). Dichloromethane (DCM, Acros Organics, Pittsburg, PA) was dried by distillation over calcium hydride. Diethyl ether, dimethylformamide (DMF) and hexane were received from VWR (Bristol, CT) and used as received. Dialysis tubing with 0.1-0.5 kDa and 3.5 kDa cutoff MW was received from Spectrum Laboratories (Rancho Dominguez, CA). N,N'-disuccinimidyl carbonate (DSC) and bovine serum albumin (BSA) were received from Novabiochem® (San Diego, CA) and Jackson ImmunoResearch (West Grove, PA), respectively. EBM™2 medium, EGM™-2 BulletKit™ medium, human basic fibroblast growth factor (bFGF), R3-insulin like growth factor-1 (IGF-1), human epidermal growth factor (EGF), ascorbic acid (AA), β-sodium glycerophosphate (βGP), dexamethasone (DEX), hydrocortisone, gentamycin sulfate (GS), penicillin (PN), streptomycin (SP), and amphotericin-B were received from Lonza (Hopkinton, Mass.). PECAM-1 (CD31) and bovine anti-rabbit IgG-FITC (secondary antibody) were received from Santa Cruz Biotechnology (Dallas, Tex.). Human VEGF, rhBMP-2 (hereafter referred to as BMP2), their Enzyme-Linked Immunosorbent Assay (ELISA) kits, and bFGF (FGF2) ELISA kit were received from MyBioSource (San Diego, CA). Human plasminogen and MMP-2 ELISA kits were received form Innovative Research (Court Novi, MI) and Boster (Pleasanton, CA), respectively. Acetomethoxy derivative of calcein (cAM) and ethidium homodimer (EthD) were received from Life Technologies™ (Grand Island, NY), and MTS cell viability assay was received from Thermo-Fisher (Waltham, MA). Quant-iT™ PicoGreen™ dsDNA reagent kit was received from Invitrogen™ (Carlsbad, CA). The kits for QuantiChrom™ calcium and alkaline phosphatase (ALP) assays were received from BioAssay Systems (Hayward, CA).

Material Synthesis: A two-step procedure was used to synthesize linear LPELA macromonomer. Acrylamide-terminated glycine-arginine-glycine-aspartic acid (Ac-GRGD (SEQ ID NO: 8)) cell-adhesive peptide was synthesized and purified. GelMA was synthesized by the reaction of gelatin with methacrylic anhydride. PEG with PEG MW of 12 kDa was chain-extended with short lactide (L) and glycolide (G) blocks (LG/PEG molar ratio of 24 and L:G ratio of 60:40); the chain-ends were terminated with succinimide groups; the macromers were assembled into NGs by dialysis; and VEGF was grafted to the NGs to generate VEGF-NGs. The grafting efficiency of VEGF to the NGs was 92±1%. VEGF was released steadily from VEGF-NGs in 7 days, measured by ELISA.

Synthesis of Plasmin Cleavable NPs: The following approach was used to synthesize the PEG-SPCP conjugate as illustrated in FIGS. 1A-1E. FIGS. 1A-1E illustrate a schematic diagram for the synthesis of a plasmin-cleavable, self-assembled, BMP2-grafted PxSPCP NP. The sequence cysteine-glycine-glycine-lysine with doubly-protected lysine residue [CGGK(α-Fmoc)(ε-MTT) (SEQ ID NO: 9)] was synthesized in the solid phase on Wang resin. The acetyl-terminated triphenylalanine with a glycine spacer (GFFF-ac_(SEQ ID NO: 10)) was synthesized separately in the solid phase on Wang resin and coupled to the MTT terminus of CGGK (SEQ ID NO: 11) to yield the CGGK (GFFF-ac)(α-Fmoc) sequence (SEQ ID NO: 12, "GFFF-ac" disclosed as SEQ ID NO: 10). After MTT deprotection, the sequence plasmin-cleavable KFKT (SEQ ID NO: 13) with two glycine spacers on each side (GGKFKTGG (SEQ ID NO: 14)) was coupled by EDC chemistry to the Fmoc terminus of CGGK(GFFF-ac)(α-Fmoc) (SEQ ID NO: 12, "GFFF-ac" disclosed as SEQ ID NO: 10) to yield the CGGK(GFFF-ac)GGKFKTGG peptide SEQ ID NO: 15, "GFFF-ac" disclosed as SEQ ID NO: 10) (SPCP) (FIG. 1A). After cleaving from the resin, the SPCP peptide was purified by high-performance liquid chromatography (HPLC) and characterized by electrospray ionization spectrometry. The peptide CGGK(GFFF-ac)GGG SEQ ID NO: 16, "GFFF-ac" disclosed as SEQ ID NO: 10) without the KFKT (SEQ ID NO: 13) sequence (SP) was synthesized to produce NPs that did not undergo cleavage in response to plasmin.

PEG with MW of 2, 5, and 7 kDa was reacted with acryloyl chloride to produce PEGDA. Next, PEGDA in PBS was added dropwise to the solution of SPCP peptide (PEGDA:SPCP molar ratio of 1:2.5) in acetonitrile/PBS (pH 7.4, 1 mM TCEP) in a reaction flask with stirring and nitrogen flow. The reaction between the cysteine groups of SPCP and acrylate groups of PEGDA was allowed to proceed for 6 hours under ambient condition. After the reaction, the PEG-SPCP conjugate was purified by dialysis (500 Da MW cutoff membrane) against PBS and lyophilized (FIG. 1B). Then, the carboxyl end-groups of PEG-SPCP conjugate were succinimide-functionalized by reaction with DSC (FIG. 1C). The chemical structure of the lyophilized PEG-SPCP conjugate was characterized by $^1$H-NMR (Varian Mercury-300, Palo Alto, Calif.) and FTIR (PerkinElmer Spectrum™ 100, Waltham, Mass.). The functionalized conjugates with and without the plasmin-cleavable peptide are hereafter referred to as PxSPCP and PxSP, respectively, where the letter "x" is the PEG MW in kDa, "SP" is for the self-assembled peptide FFF, and "CP" is for the plasmin-cleavable peptide KFKT (SEQ ID NO: 13).

To form NPs, the functionalized PxSPCP conjugates were dissolved in DMSO and self-assembled by dialysis against PBS. The NP suspension was freeze-dried to produce a free-flowing powder (FIG. 1D). The average particle size, size distribution, and zeta potential of PxSPCP NPs were measured with a Zetasizer Nano ZS dynamic light scattering (Malvern Instruments, Malvern, UK) at 25° C. in Nano-pure water (Millipore, Billerica, Mass.). To observe particle shape, 20 μL of the suspension was deposited onto a 300-mesh carbon-coated copper grid and imaged with a transmission electron microscope (Hitachi H8000, Schaumburg, Ill.).

Cell Culture: Human MSCs (Lonza, Allendale, N.J.) were cultured in basal MSC medium (high-glucose DMEM supplemented with 10% FBS, 100 units/mL penicillin and 100 μg/mL streptomycin) at a seeding density of 5000 cells/cm$^2$. Human ECFCs (Boston Children's Hospital) were cultured on 1% gelatin coated flasks in basal ECFC medium (BulletKit™ EBM™-2 medium supplemented with 20% FBS) at a density of 6500 cells/cm$^2$.

Cell Encapsulation in LPELA and GelMA Hydrogels: The LPELA precursor solution was prepared by mixing 200 mg LPELA, 4 mg Ac-GRGD (SEQ ID NO: 8) cell-adhesive peptide (2% by weight of LPELA) and 1.5 mg photo-initiator (0.75 wt %) in 1 mL PBS. After sterilization by filtration, hMSCs at a density of 2×106 cells/mL were added to the sterile LPELA solution, the suspension was injected between two sterile glass slides separated by a spacer and crosslinked by UV irradiation. The GelMA precursor solution was prepared by mixing 50 mg GelMA and 0.375 mg photo-initiator (0.75 wt %) in 1 mL PBS. After sterilization by filtration, a 50:50 mixture of hMSCs+ECFCs at a total density of 2×106 cells/mL were added to the sterile GelMA solution, injected between two sterile glass slides separated by a spacer and crosslinked by UV irradiation. After washing with PBS, the cell-encapsulated LEPLA or GelMA hydrogels were cultured in the appropriate medium for osteogenic or vasculogenic differentiation, respectively.

Grafting BMP2 to PxSPCP NPs and Protein Release: BSA was grafted to PxSPCP NPs for particle size analysis, grafting efficiency and protein stability studies whereas BMP2 was grafted for protein release and cell culture experiments. For grafting, 10 mg PxSPCP NPs were dispersed in PBS by sonication for 5 minutes. Next, 0.5 mL of BMP2 (400 ng/mL) or BSA (20 mg/mL) were added to the NP suspension and the grafting reaction between the free amine groups of BMP2 or BSA and the succinimide groups of the NPs was allowed to proceed overnight under ambient condition to produce BMP2-PxSPCP NPs (FIG. 1E). After the reaction, the suspension was centrifuged at 15000 rpm for 10 minutes and the amount of free (not grafted) BMP2 or BSA in the supernatant was quantified by ELISA or BCA protein assay, respectively.

For release studies, plasmin (0.2 U/mL) was added to the suspension of 10 mg BMP2-PxSPCP NPs in 1 mL PBS and incubated at 37° C. with shaking at 50 rpm. At each time point, the suspension was centrifuged at 10,000 rpm for 5 minutes, the supernatant containing the free BMP2 was collected and replaced with fresh plasmin solution. BMP2 content of the supernatant solution was measured with a BMP2 ELISA kit. BMP2 added directly to the plasmin solution and BMP2-PxSP NPs were used as control groups.

Bioactivity and Cell Compatibility of BMP2-PxSPCP NPs: Circular dichroism (CD) was used to determine the effect of grafting on secondary structure of the model BSA protein. CD spectra of free or grafted BSA in PBS were collected with a spectropolarimeter (JASCO J815, Essex, UK) at 20° C. with a cuvette of 0.1 cm path length. For evaluation of cell compatibility, hMSCs (1×106 cells/mL) and PxSPCP NPs (10 mg) were encapsulated in LPELA hydrogel and cultured in basal medium. At each time point, the hydrogels were stained with cAM/EthD live/dead assay (1 μg/mL) and the stained cells were imaged with an inverted fluorescent microscope (Nikon Eclipse Ti-ε, Nikon, Melville, N.Y.). To quantify cell viability, the medium was replaced with fresh medium containing 10% MTS and incubated for 6 hours at 37° C. and the sample absorbance was measured with a microplate reader (Molecular Devices, San Jose, Calif.) at a wavelength of 490 nm.

The bioactivity of BMP2 released from the NPs was determined by measuring the expression of osteogenic markers for hMSCs encapsulated in LPELA hydrogel and incubated in the osteogenic medium (without BMP2 or DEX) supplemented with BMP2 released from the NPs. The measured markers of osteogenic differentiation included RUNX2 (early marker) and calcium (late marker). Control groups included hMSCs encapsulated in LPELA hydrogel and incubated in osteogenic medium with or without BMP2 directly added to the medium.

Measurement of Protease Expression of Encapsulated hMSCs and ECFCs: hMSCs at a density of 2×106 cells/mL were encapsulated in LPELA hydrogel, whereas ECFCs or a 50:50 mixture of hMSCs+ECFCs at a total density of 2×106 cells/mL were encapsulated in GelMA hydrogel as described. After gelation, disk-shape samples were cut from the gels and incubated in the appropriate medium for up to 7 days. hMSCs encapsulated in LPELA were cultured in osteogenic medium, whereas ECFCs or hMSCs+ECFCs in GelMA were cultured in vasculogenic medium. At each time point, samples were divided into two parts for analysis. One part was used for measurement of differential RNA expression of plasminogen, uPA, tPA, matrix metalloproteinase-2 (MMP-2), and membrane-type matrix metalloproteinase-1 (MT-MMP-1) by real-time polymerase chain reaction (RT-qPCR.) The gene specific primers for RT-qPCR were designed and selected using the Primer3 web-based software. The forward and reverse primers, synthesized by Integrated DNA Technologies™ (Coralville, Iowa), are listed in Table 1. The expression of GAPDH house-keeping gene was used as a reference and the model of Pfaffl was used to determine the expression ratio of the genes. The other part was used to quantify protein expression of the total plasmin and MMP-2 in the intracellular and extracellular compartments as well as the extracellular expression of bFGF. To quantify the extracellular expressions, the medium of the hydrogel cultures was centrifuged at 15000 rpm for 10 minutes to separate the insoluble residue; the supernatant was concentrated 5-fold using a 10 kDa cutoff membrane; and the protein concentration was measured by ELISA. To quantify the intracellular expressions, the hydrogel sample was washed, digested in RIPA buffer, centrifuged at 15000 rpm for 15 minutes, and the concentration of proteins in the supernatant was measured by ELISA.

Figure 2:
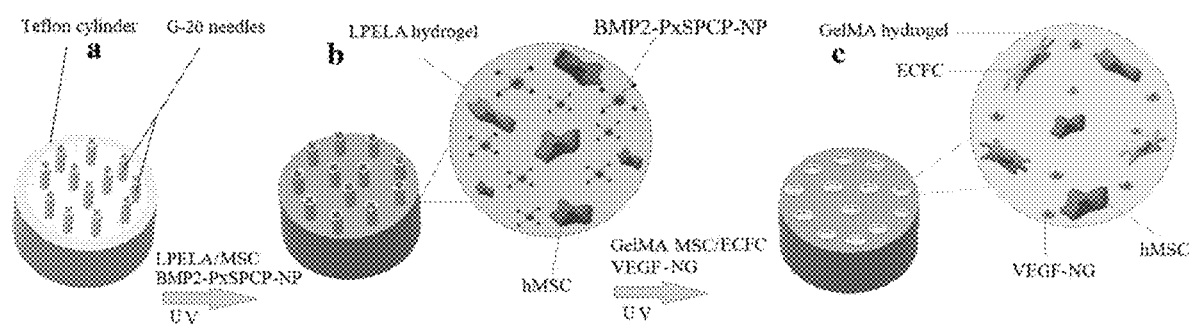
FIG. 2 illustrates an example system for use with exemplary embodiments of the disclosure.

Encapsulation of hMSCs and ECFCs in Patterned Constructs: Patterned hydrogel constructs with GelMA microchannels in LPELA matrix were generated for co-culture experiments (FIG. 2). FIG. 2 displays a schematic diagram for generating the patterned cellular constructs. The LPELA hydrogel precursor solution loaded with hMSCs and BMP2-PxSPCP NPs was injected inside a Teflon® cylinder fitted with needles. After LPELA gelation, needles were removed and the GelMA precursor solution loaded with ECFCs+ hMSCs and VEGF-NGs was injected in the microchannels and crosslinked. The constructs were cultured in appropriate medium with time and analyzed with respect to the expression of markers for osteogenesis and vasculogenesis.

Needles with a diameter of 400 μm and inter-needle separation of 500 μm were inserted through the endcaps of a cylindrical Teflon® mold with diameter and height of 5 and 3 mm, respectively (FIG. 2). Next, the sterile LPELA precursor suspension composed of 200 mg LPELA, 4 mg Ac-GRGD (SEQ ID NO: 8) cell-adhesive peptide, 1.5 mg photo-initiator, 20 mg plasmin-cleavable PxSPCP NPs, and $2\times10^6$ hMSCs in 1 mL PBS was injected in the cylindrical mold and crosslinked by UV irradiation. Then, the needles were removed from the LPELA matrix, and the sterile GelMA precursor suspension composed of 50 mg GelMA, 0.375 mg photo-initiator, 2 mg VEGF-NGs, $2\times10^6$ of 50:50 hMSCs+ECFCs was injected in the channels and crosslinked by UV irradiation. After gelation, the patterned hydrogel constructs were washed with warm PBS, cultured in basal medium for one day, followed by cultivation in vasculogenic medium (without VEGF) for days 2-7, 50:50 mixture of vasculogenic and osteogenic medium (without VEGF, BMP2 or DEX) for days 8-10, and finally in osteogenic medium (without DEX or BMP2) for days 11-21.

Biochemical, mRNA and Protein Analysis and Immunofluorescent Staining: At each time point after washing the hydrogel constructs to remove serum proteins and sonicating to lyse the encapsulated cells, 43 samples were divided into four groups for biochemical, mRNA and protein analysis, and immunofluorescent staining. For biochemical analysis, the double-stranded DNA content, ALP activity, and calcium content of the homogenized samples were measured. For mRNA expression, the RNA of the homogenized samples was extracted and used for measurement of mRNA expression of osteogenic markers (RUNX2, Col I, and ALP) and vasculogenic markers (vWF, VEGFR, VE-cadherin, and CD31). To compare expression between the groups, mRNA-fold difference for expression of the gene of interest was normalized to that of GAPDH, followed by normalization against day one expression. The expression of CD31 vasculogenic marker of the homogenized samples at the protein level was quantified by western blot. Alizarin red and immunofluorescent staining were used to image the intensity of mineralization and CD31 expression. The stained samples were imaged with a Nikon Eclipse Ti-ε inverted fluorescent microscope.

Statistical Analysis: All experiments were done in triplicate. Significant differences between experimental groups were evaluated using a two-way ANOVA™ with replication test, followed by a two-tailed Student's t test. A value of $p<0.05$ was considered statistically significant.

Results

Figure 3D:
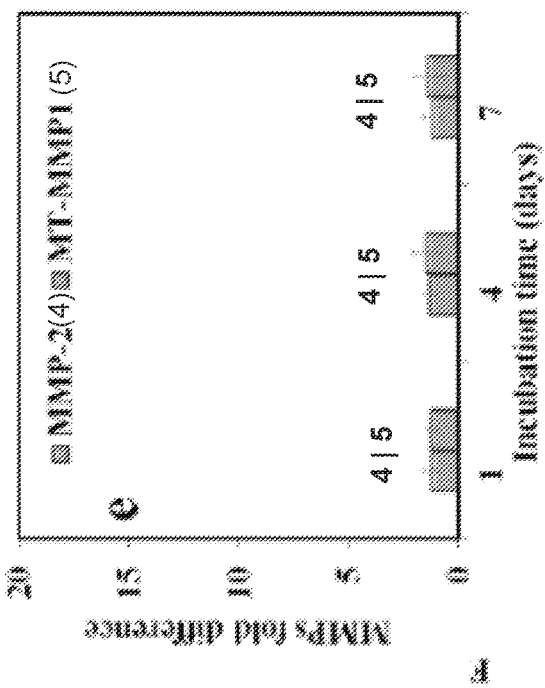
Figure 3E:
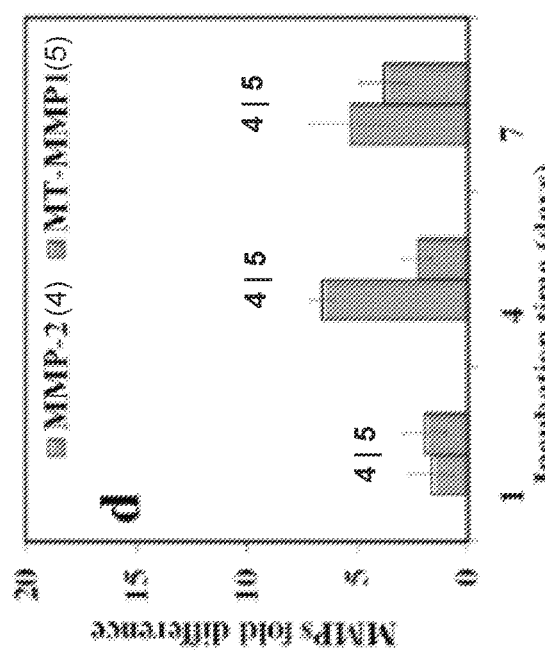
Figure 3F:
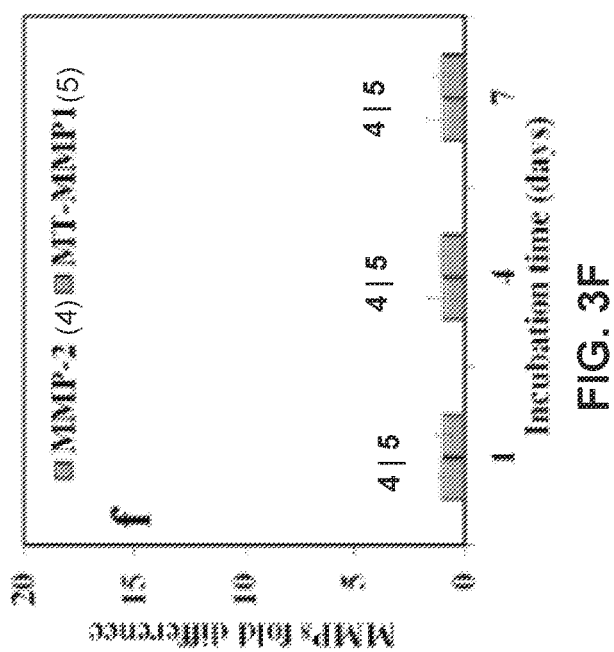

Temporal Expression of Proteases by the Encapsulated hMSCs and ECFCs: The mRNA expressions of uPA, tPA, and plasminogen in the fibrinolytic cascade for the LPELA encapsulated MSCs, GelMA encapsulated ECFCs, and GelMA encapsulated MSCs+ECFCs with incubation time are shown in FIGS. 3A, 3B, and 3C, respectively; the mRNA expressions of MMP-2 and MT-MMP-1 for the encapsulated MSCs, ECFCs, and MSCs+ECFCs are shown in FIGS. 3D-3F, respectively. The encapsulated hMSCs expressed significant levels of uPA, tPA, plasminogen, MMP-2, and MT-MMP-1 in osteogenic medium (days 1, 4, and 7) as shown in FIGS. 3A and 3D. The expression of uPA by MSCs did not change with differentiation in osteogenic medium, whereas that of tPA decreased, those of plasminogen and MMP-2 increased, and that of MT-MMP-11 peaked on day 4. The encapsulated ECFCs did not express significant levels of proteases of the fibrinolytic cascade and the expressions did not change with differentiation in vasculogenic medium (FIGS. 3B and 3E). The encapsulated hMSCs+ECFCs expressed significant levels of tPA and plasminogen with differentiation in vasculogenic medium but did not express uPA, MMP-2 and MT-MMP-1. The expression of tPA of hMSCs+ECFCs peaked on day 4, whereas that of plasminogen increased slightly with differentiation in the vasculogenic medium.

Based on mRNA results, the extra- and intra-cellular expressions of plasmin and MMP-2, as well as extracellular expression of bFGF for the encapsulated hMSCs, ECFCs, and hMSCs+ECFCs, were measured at the protein level and the expressions are shown in FIG. 4. FIG. 4 displays extra- and intra-cellular protein expressions for MMP-2 (FIGS. 4A-4B), total plasmin (FIGS. 4C-3D), and the extra-cellular protein expression of bFGF (FIG. 4E) for MSCs (square, 6), ECFCs (diamond, 7), and MSCs+ECFCs (triangle, 8). MSCs were encapsulated in LPELA hydrogel and cultured in osteogenic medium whereas ECFCs and MSCs+ECFCs were encapsulated in GelMA and cultured in vasculogenic medium.

Figure 4A:
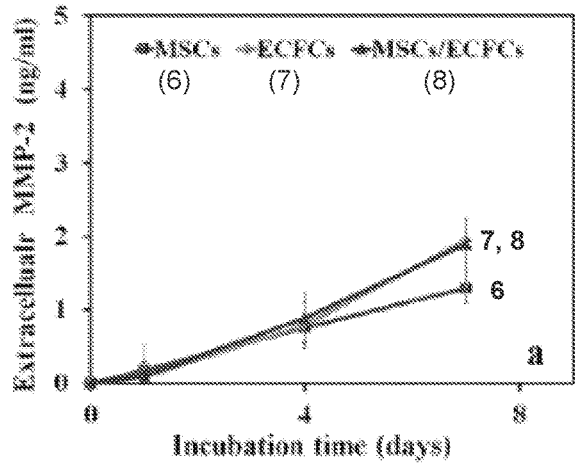
FIGS. 4A-4E illustrate line graphs showing intracellular (4B and 4D) or extracellular (4A, 4C, and 4E) release of a protein in accordance with exemplary embodiments of the disclosure.
Figure 4B:
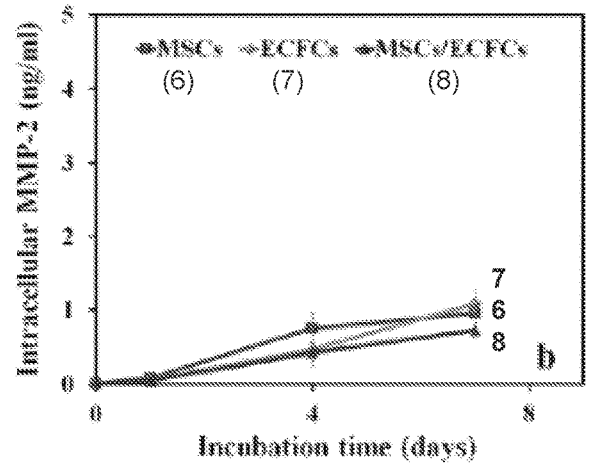
Figure 4C:
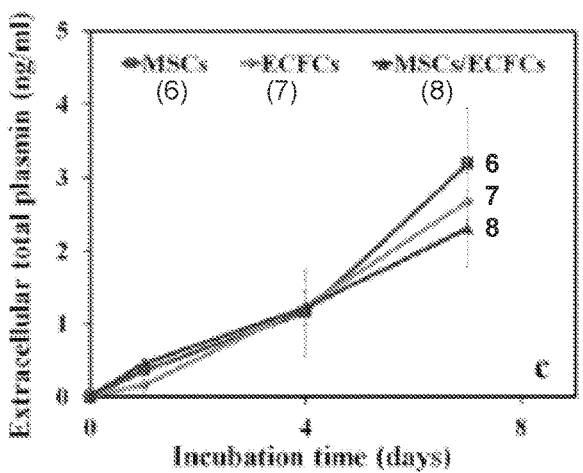
Figure 4D:
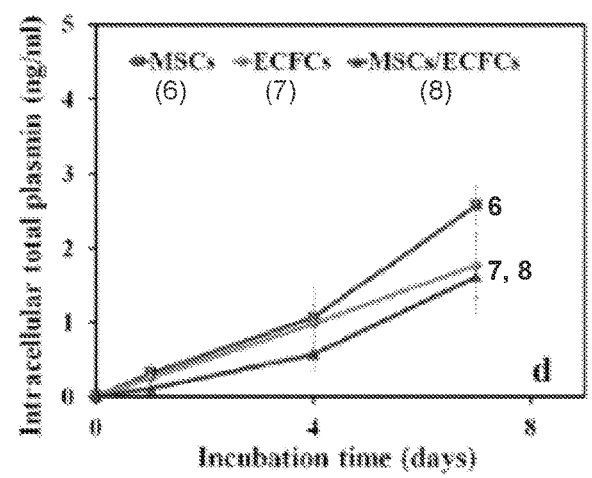
Figure 4E:
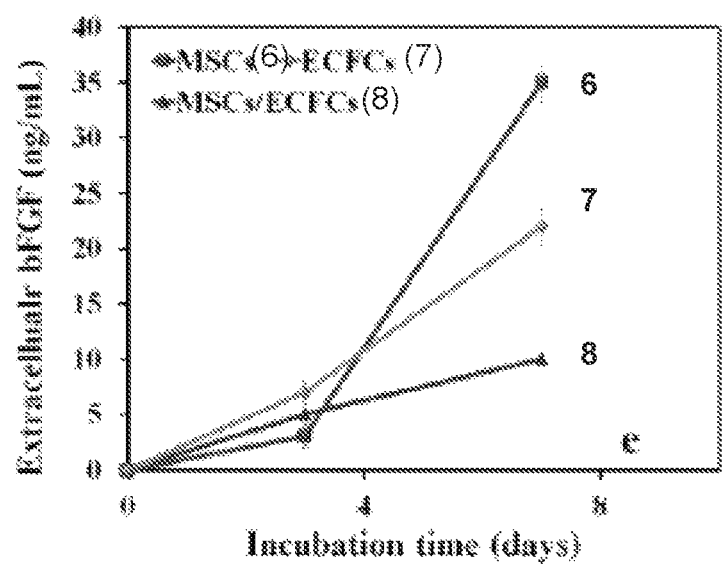
Figure 5B:
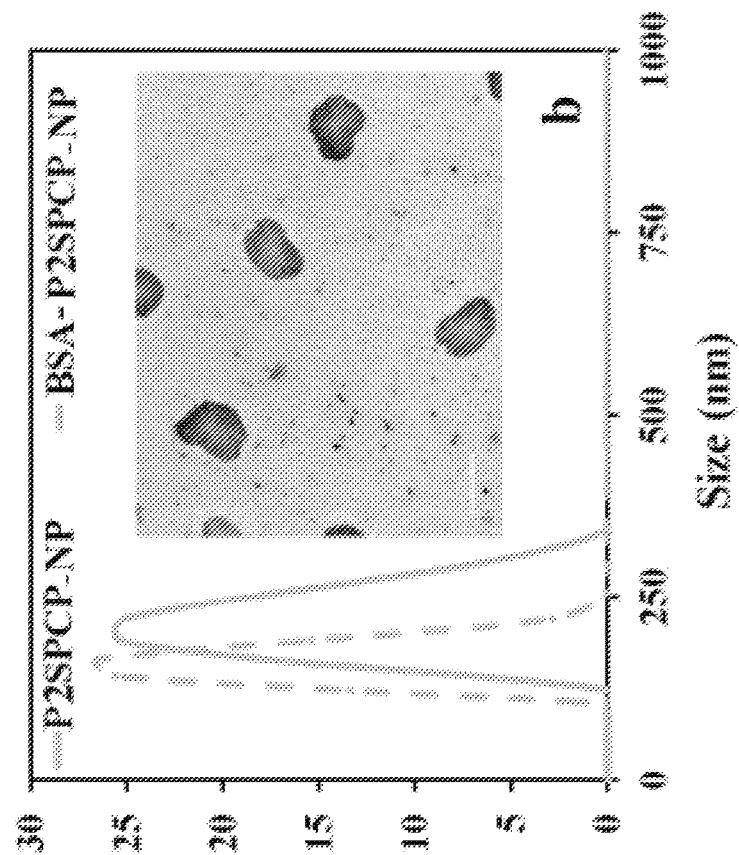
FIGS. 5A-5D illustrate images and histograms displaying particle size of nanoparticles formed from a hybrid multifunctional macromer in accordance with exemplary embodiments of the disclosure.
Figure 5A:
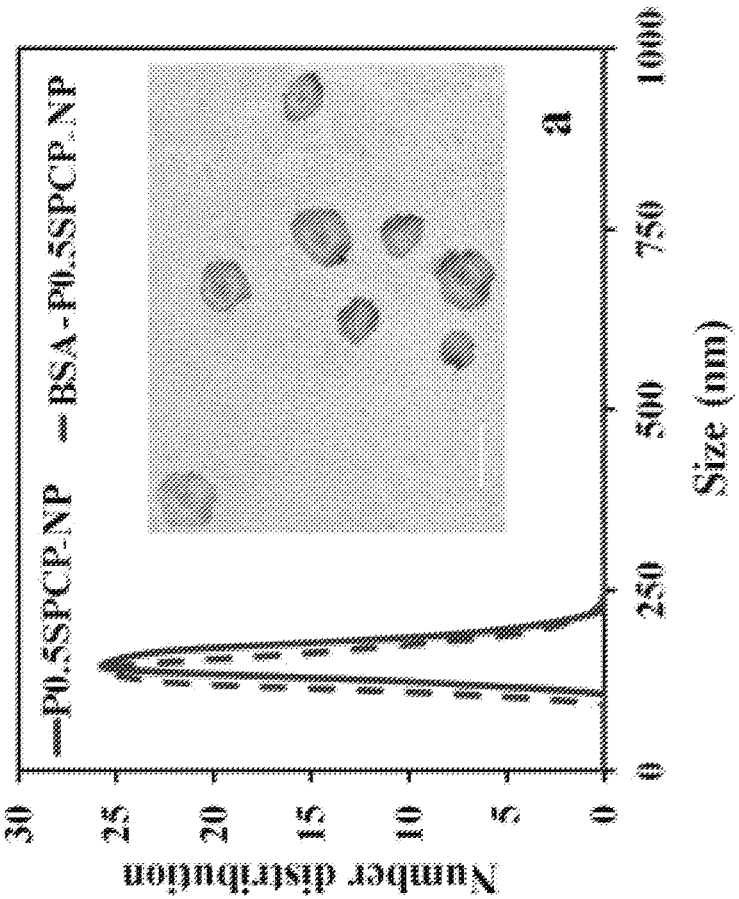
Figure 5D:
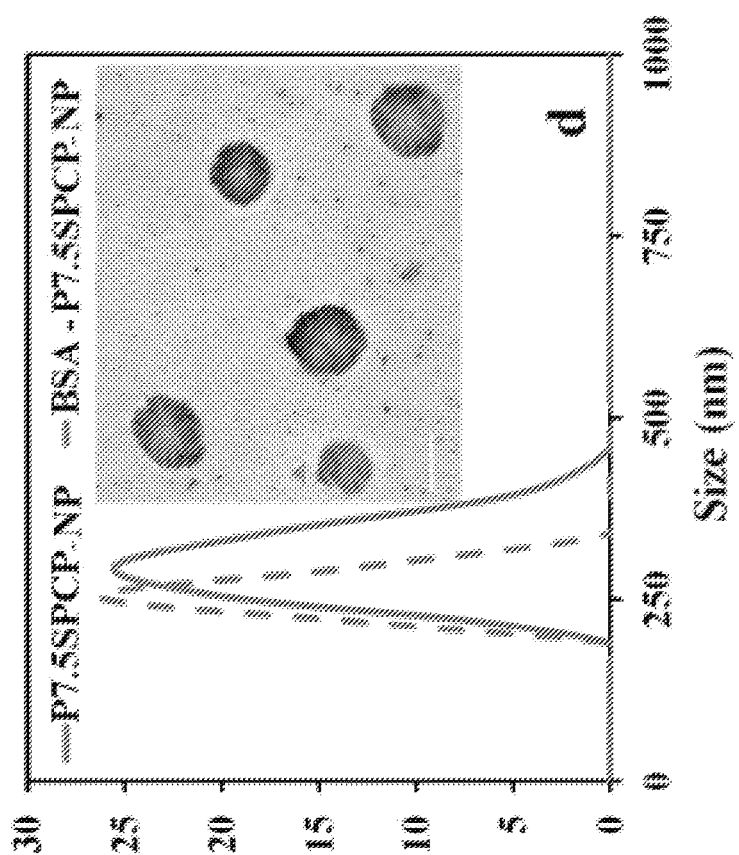
Figure 5C:
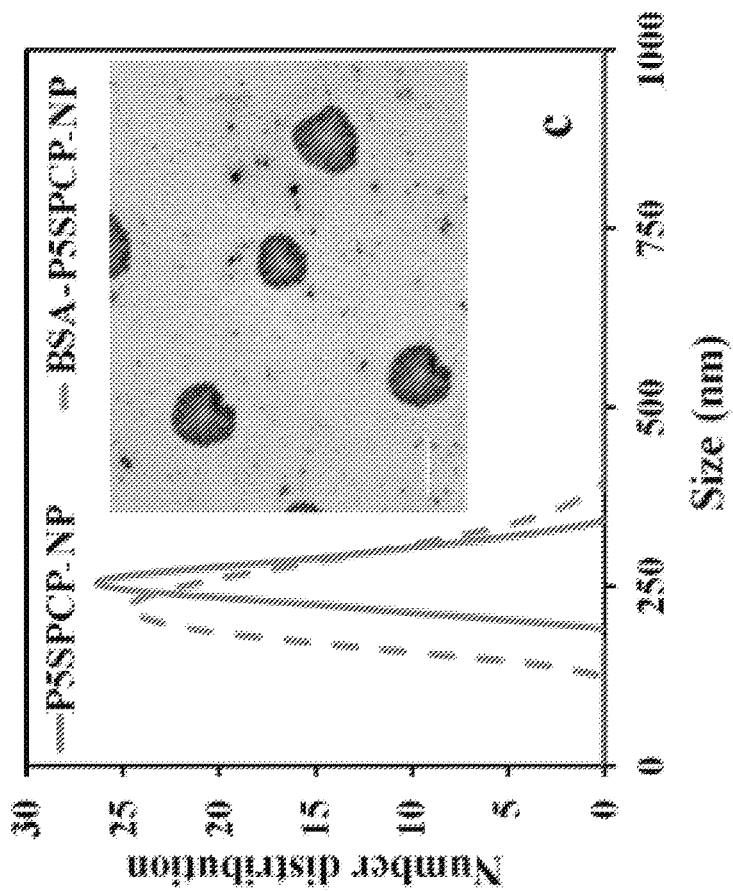

For all cell types, the expressions of plasmin, MMP-2 and bFGF increased with cell differentiation. For all cell types, the extracellular expression of MMP-2 was higher than the intracellular (FIGS. 4A and 4B), whereas the difference was not significant for plasmin (FIGS. 4C and 4D). After 7 days of culture, the extracellular expression of bFGF by the encapsulated hMSCs in osteogenic medium was higher than the ECFCs or hMSCs+ECFCs in vasculogenic medium with hMSCs+ECFCs showing the lowest bFGF expression (FIG. 4E). Based on the results in FIGS. 3A-3F and FIGS. 4A-4E, the encapsulated hMSCs showed higher expression of proteases with differentiation in osteogenic medium as compared to ECFCs or hMSCs+ECFCs in vasculogenic medium. Therefore, BMP2 was conjugated to plasmin-cleavable PxSPCP NPs and co-encapsulated with hMSCs in LPELA hydrogel of the patterned matrix for on-demand release of BMP2 in response to plasmin expression by hMSCs. As plasmin and MMP-2 expression by the encapsulated hMSCs+ECFCs was relatively low, VEGF was conjugated to hydrolytically degradable NGs and co-encapsulated with hMSCs+ECFCs in GelMA hydrogel of the patterned matrix for release in the first 7 days to stimulate vasculogenic differentiation of the encapsulated ECFCs in the channels.

Characterization of PxSPCP macromer: The mass spectra of CGGK(GFFF-ac)GGKFKTGG SEQ ID NO: 15, "GFFF-ac" disclosed as SEQ ID NO: 10) (SPCP, MW=1638.9 Da) and CGGK(GFFF-ac)GGG SEQ ID NO: 16, "GFFF-ac" disclosed as SEQ ID NO: 10) (SP, MW=1018.2 Da) polypeptides were determined. In the SPCP spectrum, m/z values of 820 and 1638 Da corresponded to the divalent [(M+2H)]2+ and monovalent [(M+H)]+1 hydrogen cations of the peptide, respectively. In the SP spectrum, m/z value of 1018 Da corresponded to the monovalent [(M+H)]+hydrogen cation of the peptide. The retention times of SPCP and SP peptides were 10.1 minutes and 11.0 minutes, respectively. The $^1$H-NMR spectra of PEGDA and PEG-SPCP-NHS (PxSPCP) were also obtained. Two chemical shifts with peak positions at 3.6 and 4.2 ppm in the spectrum of PEGDA were attributed to the methylene hydrogens of PEG attached to ether and ester groups, respectively; three chemical shifts with peak positions between 5.85-6.55 ppm were attributed to vinyl hydrogens of the acrylate groups at chain ends. The disappearance of chemical shifts for methylene protons (5.85-6.55 ppm) of the acrylate groups in the spectrum of PxSPCP confirmed conjugation of the peptide to PEGDA. Further, the appearance of a shift due to methylene hydrogens with peak position at 2.77 ppm confirmed succinimide functionalization of PxSPCP. The FTIR spectra of PEGDA, PEG-SPCP, and PEG-SPCP-NHS were obtained. The appearance of characteristic absorption bands in the spectra of PEG-SPCP and PEG-SPCP-NHS with peak positions at 1630 and 3330 cm$^{-1}$ due to vibrations of amides and secondary amines, respectively, confirmed the conjugation of peptide to PEGDA. The appearance of a characteristic band with peak position at 1779 cm$^{-1}$ due to vibrations of NHS group confirmed succinimide functionalization of PEG-SPCP-NHS.

Characterization of PxSPCP NPs: The number-average size distribution of PxSPCP NPs with or without BSA protein grafting for PEG MW of 0.5 kDa, 2 kDa, 5 kDa, and 7.5 kDa are shown in FIGS. 5A-5D, respectively. The corresponding TEM images of the NPs are shown in the inset of FIGS. 5A-5D. The average particle size, polydispersity index (PDI), and zeta potential of PxSPCP NPs as a function of PEG MW are listed in Table 1. The average size of the NPs increased from 145±15 nm to 225±10, 265±20 and 325±25 nm as the PEG MW was increased from 0.5 kDa to 2 kDa, 5 kDa, and 7.5 kDa, respectively. The size distribution of the NPs was relatively narrow and increased with PEG MW. The average size of P0.5SPCP NPs increased slightly after BSA grafting and the size increase with BSA grafting increased with PEG MW.

Figure 6C:
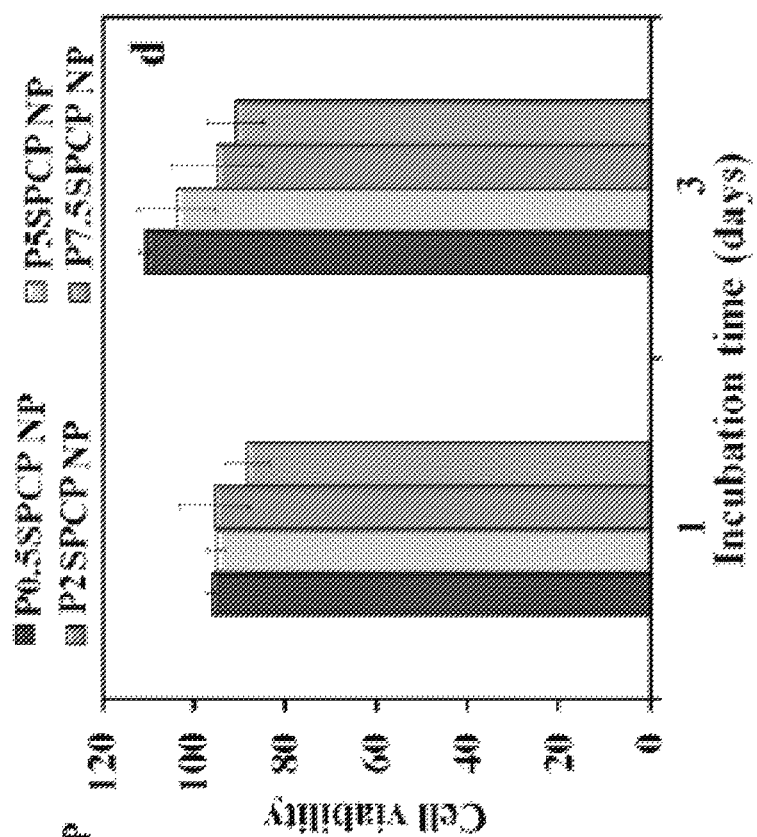

The effect of incubation time in basal culture medium on the average size and size distribution for different PEG MW of PxSPCP NPs is shown in FIGS. 6A and 6B, respectively. FIGS. 6A-6D display average particle size distribution (6A) and polydispersity index (PDI) (6B) measured by dynamic light scattering (DLS) for P0.5SPCP (diamond), P2SPCP (square), P5SPCP (circle), and P7.5SPCP (triangle) NPs with incubation time. Also shown are CD spectra (6C) of BSA grafted to P0.5SPCP, P2SPCP, P5SPCP, and P7.5SPCP NPs and free BSA. The viability of hMSCs incubated in basal medium (6D) are shown under conditions supplemented with P0.5SPCP (black), P2SPCP (lighter gray), P5SPCP (gray) and P7.5SPCP (light gray) NPs. Error bars correspond to means ±1 SD for n=3.

Figure 6D:
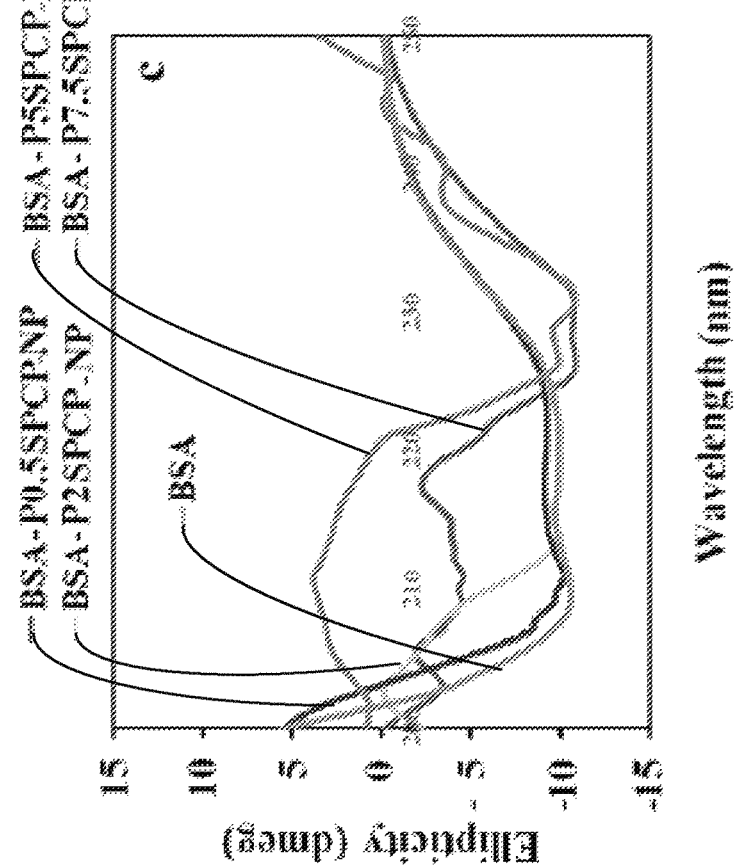

For P0.5SPCP NPs, the hydrodynamic size increased significantly from 200 nm on day 1 to 500 nm on day 7, and PDI increased from 0.13 on day 1 to 0.38 on day 7, which was attributed to particle aggregation. For P2SPCP NPs, the average size increased slightly from 225 nm on day 1 to 260 nm on day 7, and PDI did not change with incubation time. For P5SPCP and P7.5SPCP NPs, the average size and PDI did not change with incubation time. The results in FIGS. 6A and 6B indicate that P0.5SPCP NPs aggregated in culture medium, whereas P2SPCP, P5SPCP, and P7.5SPCP were relatively stable in culture medium with incubation. The effect of BSA grafting on the CD spectrum of PxSPCP NPs as a function of PEG MW is shown in FIG. 6C. The absorption spectrum of BSA-P0.5SPCP NPs was close to that of free BSA, whereas there was a slight change in absorption spectrum of BSA-P2SPCP NPs in the 200-125 nm region. The CD spectra of BSA-P5SPCP and BSA-P7.5SPCP were substantially different from that of free BSA. Therefore, the conformational stability of the grafted BSA decreased with increasing PEG MW of the NPs. Based on the CD results, P0.5SPCP and P2SPCP maintained the secondary structure of grafted BSA, whereas P5SPCP and P7.5SPCP denatured the grafted protein. The effect of supplementing the culture medium with PxSPCP NPs of different PEG MW on viability of hMSCs is shown in FIG. 6D. The viability of hMSCs decreased slightly with increasing PEG MW after 3 days of incubation in basal medium. However, viability of hMSCs was >90% for all PxSPCP NPs. Since PEG2SPCP NPs had a relatively stable size distribution in culture medium (FIGS. 6A and 6B), only a slight effect on the secondary structure of grafted BSA (FIG. 6C), and negligible toxicity toward hMSCs (FIG. 6D), these NPs were selected for vascularized osteogenesis experiments with hMSCs and ECFCs in the patterned hydrogels.

Figure 7A:
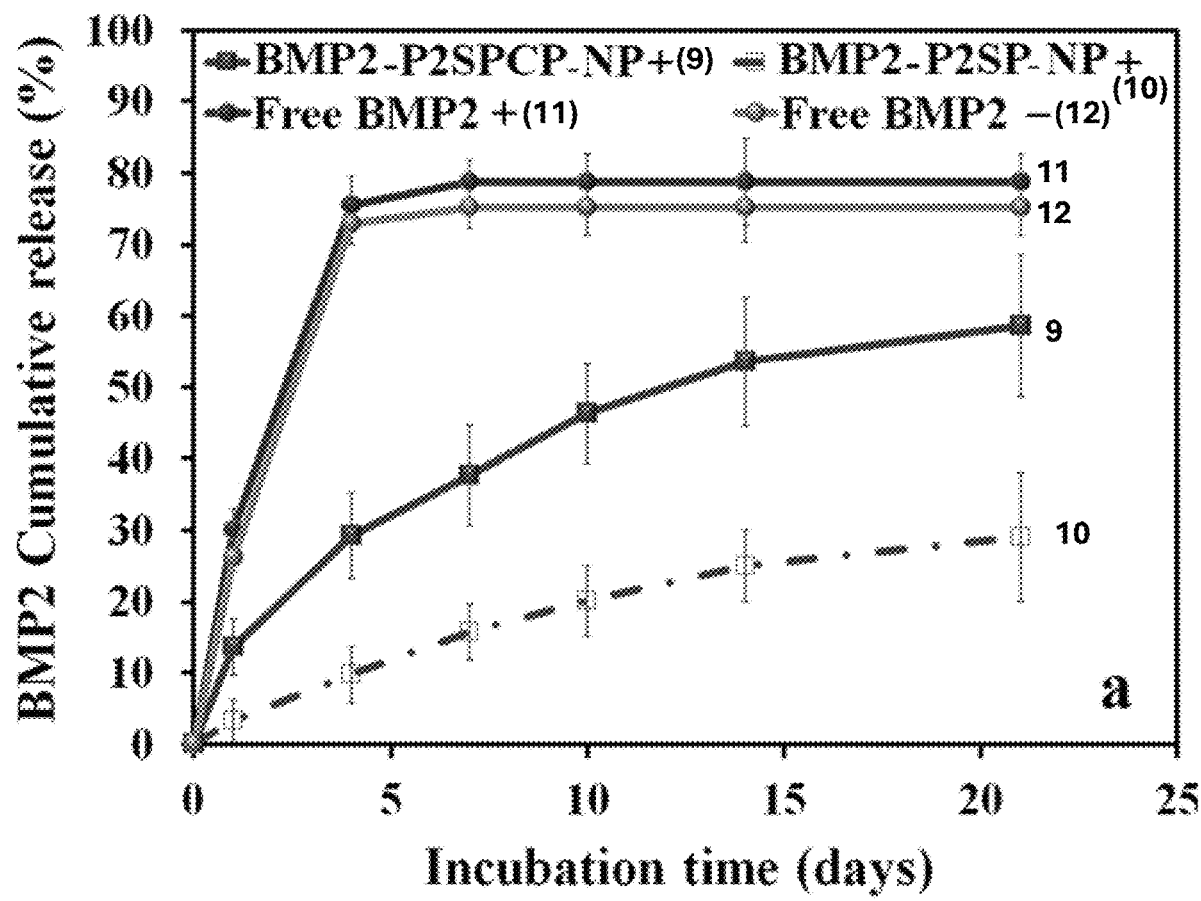
FIGS. 7A-7C illustrate line graphs displaying the cumulative release of an example protein after an incubation time in accordance with exemplary embodiments of the disclosure.
Figure 7B:
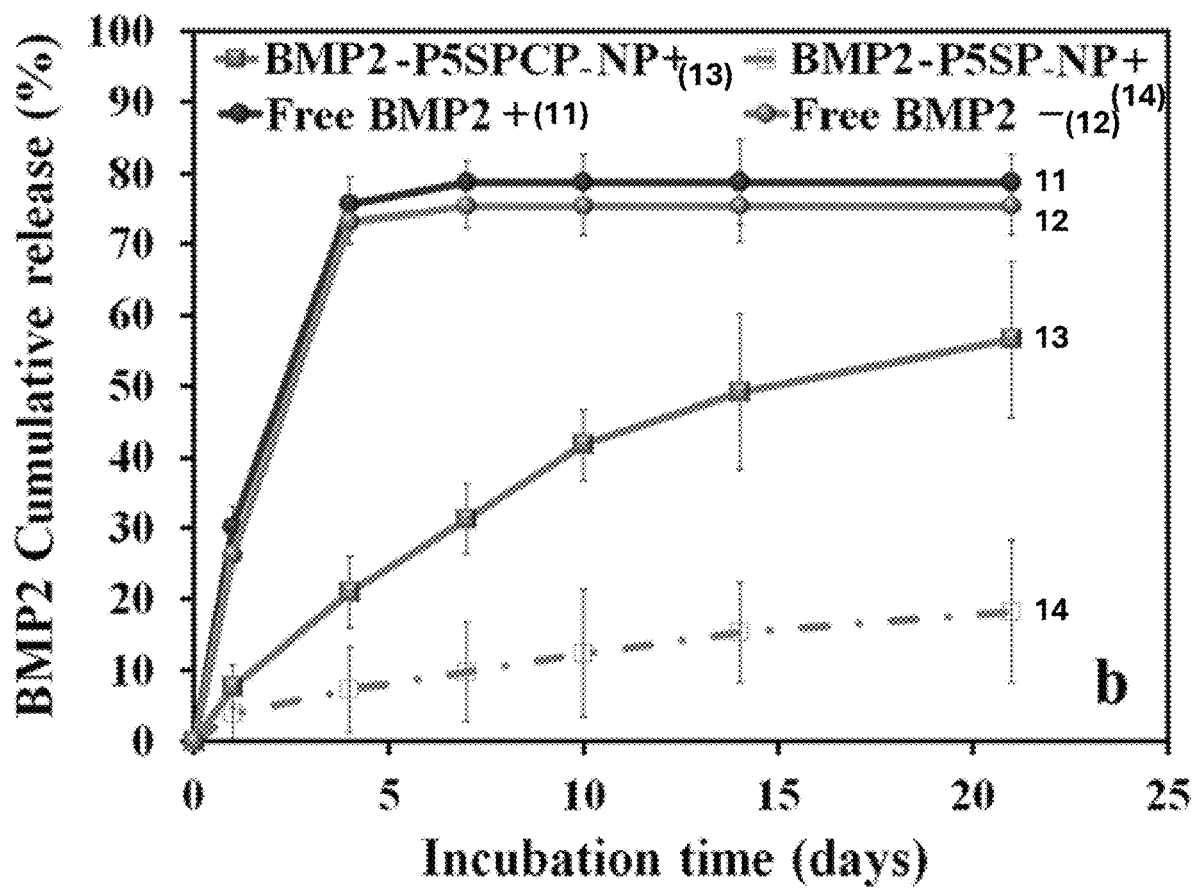
Figure 7C:
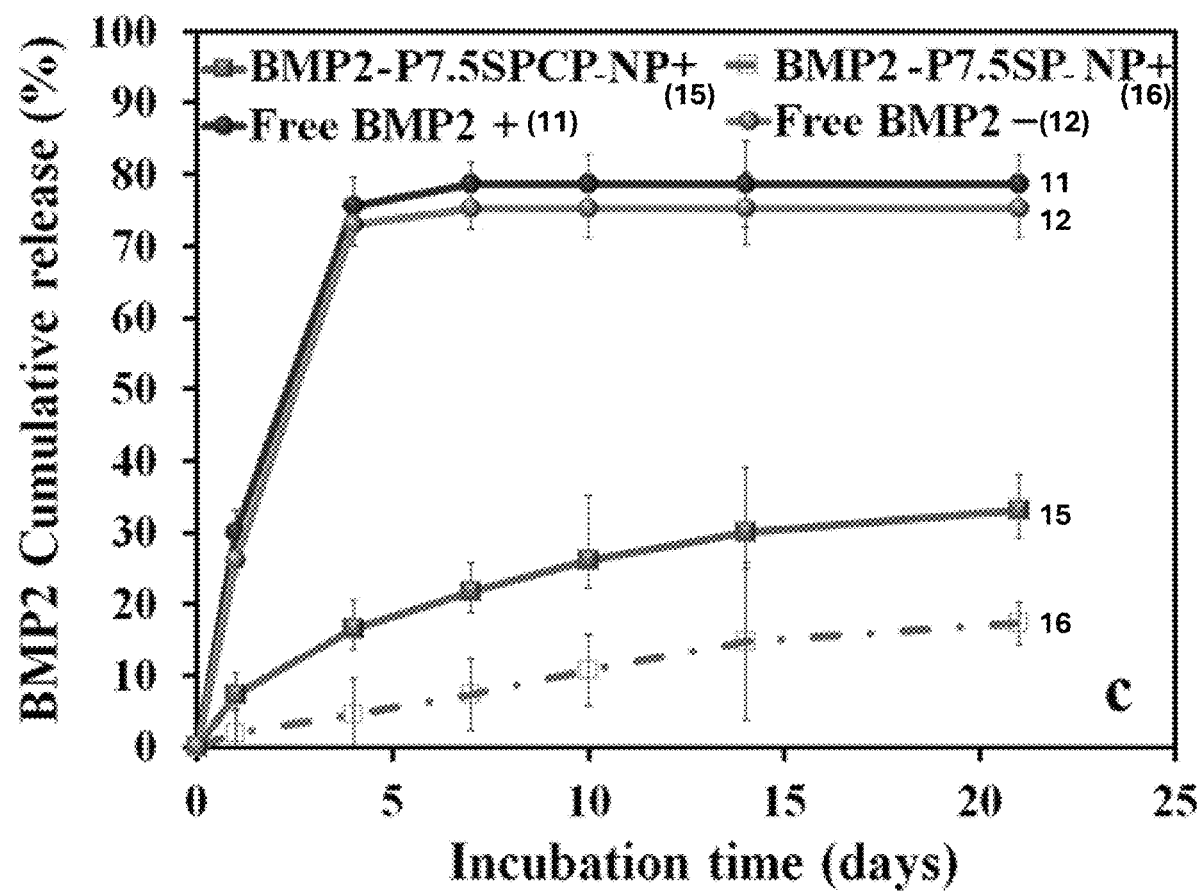

Release Characteristics and Bioactivity of BMP2-PxSPCP NPs: The grafting efficiency of BMP2 to PxSPCP NPs decreased from 73.1±2.7% to 69.5±3.2% and 24.5±1.4% as the PEG MW was increased from 2 kDa to 5 kDa and 7.5 kDa, respectively. This decrease was attributed to higher entrapment of the reactive succinimide groups of PxSPCP within the NPs' core with increasing PEG MW, which reduced their availability for BMP2 grafting. BMP2-PxSPCP NPs were encapsulated in LPELA hydrogel, the hydrogel was incubated in PBS, and the release of BMP2 to the incubating medium was measured with time by ELISA. FIGS. 7A-7C show the release kinetic of BMP2 from the encapsulated NPs in LPELA hydrogel with PxSPCP PEG MW of 2 kDa (FIG. 7A), 5 kDa (FIG. 7B), and 7.5 kDa (FIG. 7C), respectively. FIG. 7 displays (A) The cumulative release kinetics of BMP2 from BMP2-P2SPCP (square, 9) and BMP2-P2SP NPs (dashed, 10) encapsulated with plasmin in LPELA hydrogel with incubation time; (B) release of BMP2 from BMP2-P5SPCP (square, 13) and BMP2-P2SP NPs (dashed, 14) encapsulated with plasmin in the hydrogel; and (C) release of BMP2 from BMP2-P7.5SPCP (square, 15) and BMP2-P2SP NPs (dashed, 16) encapsulated with plasmin in the hydrogel. The additional lines in (FIGS. 7A-7C) provide the release of free BMP2 with (circle, 11) and without (circle, 12) plasmin from LPELA hydrogel; the + and − signs correspond to with and without plasmin, respectively. Error bars correspond to means ±1 SD for n=3.

Experimental groups included BMP2-PxSPCP NPs plus plasmin encapsulated in the hydrogel (9, 13, 15 in FIGS. 7A-7C, respectively), BMP2-PxSP NPs plus plasmin in the hydrogel (dash 10, dash 14 or dash 16 in FIGS. 7A-7C, respectively), free BMP2 in the hydrogel (11), and free BMP2 plus plasmin in the hydrogel (12). Approximately 80% of the loaded free BMP2 was released from the hydrogel after 21 days of incubation; the addition of plasmin to the hydrogel did not affect BMP2 release. The incomplete (<100%) release of free BMP2 from the hydrogel was attributed to protein adsorption to the matrix or protein denaturation during hydrogel encapsulation and gelation. ELISA measurements detected relatively small but significant BMP2 activity with incubation time for BMP2-PxSP NPs and plasmin encapsulated in the hydrogel (see 10, 14, or 16 in FIGS. 7A-7C), but the activity decreased with increasing PEG MW of the NPs. The cumulative BMP2 activity after 21 days associated with the encapsulated BMP2-PxSP NPs with PEG MW of 2 kDa, 5 kDa, and 7.5 kDa was 30%, 20% and 19% of the total BMP2 loaded in the hydrogel, respectively. This BMP2 activity was attributed to the release of BMP2-PxSP NPs from the hydrogel which was subsequently detected by ELISA. The BMP2 grafted to PxSPCP NPs and co-encapsulated in the hydrogel with plasmin was gradually released to the medium with incubation time at a rate faster than BMP2-PxSP NPs but slower than the free BMP2. For example, the cumulative release of BMP2 from the encapsulated BMP2-P5SPCP NPs was 60% after 21 days which was higher than the encapsulated P5SP NPs at 20% and slower than the free BMP2 at 80%. The results in FIGS. 7A-C demonstrate that BMP2 was cleaved by plasmin from PxSPCP NPs, leading to the gradual release of the protein from the hydrogel.

Figure 8A:
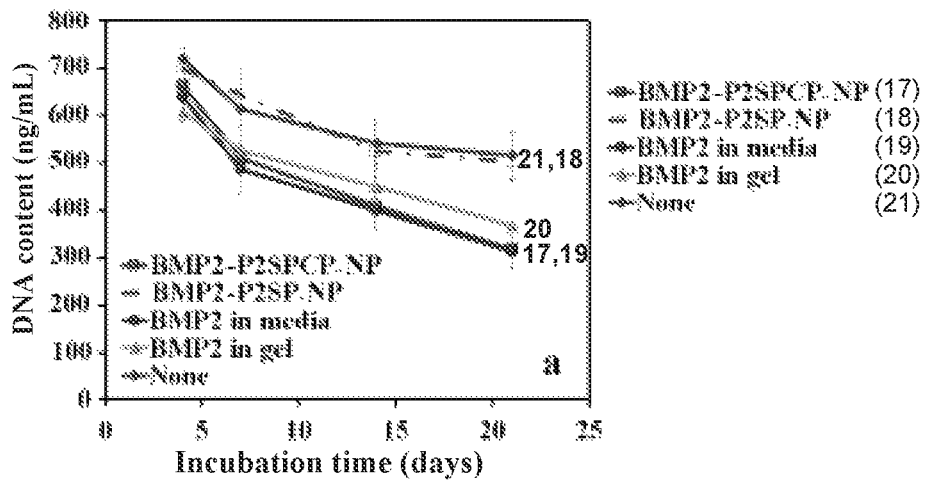
FIGS. 8A-8I illustrate graphs displaying DNA content (8A-8C), RUNX2 fold expression (8D-8F), and ALP fold expression (8G-8H) versus incubation time in accordance with exemplary embodiments of the disclosure.
Figure 8B:
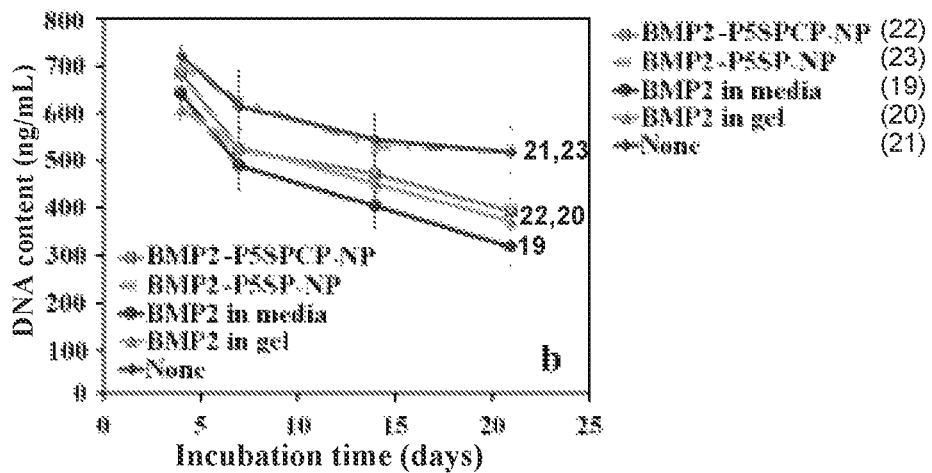
Figure 8C:
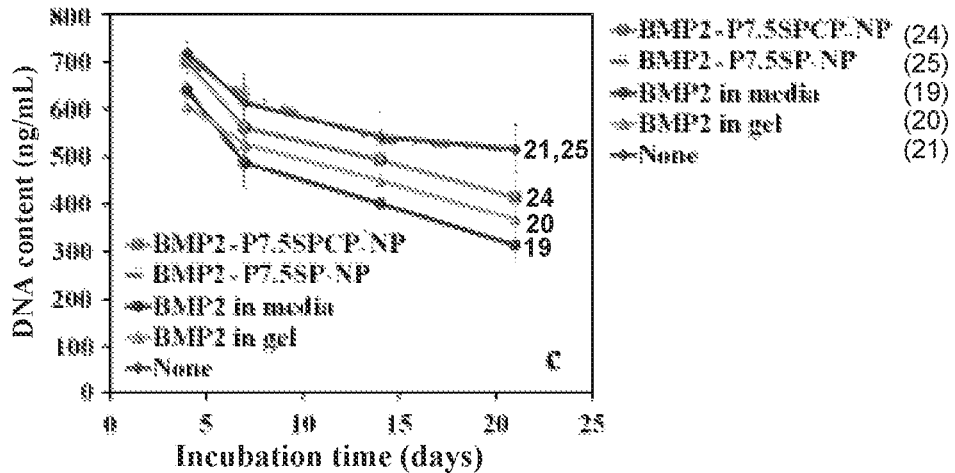
Figure 8D:
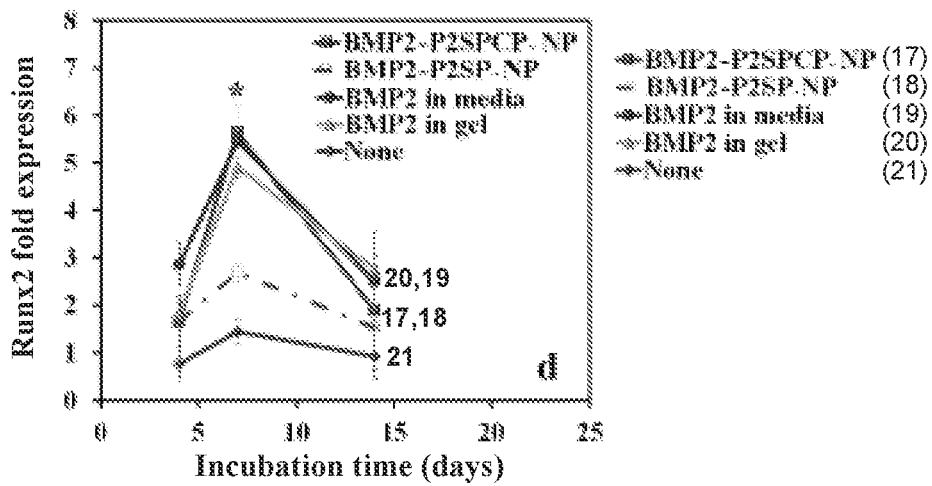
Figure 8E:
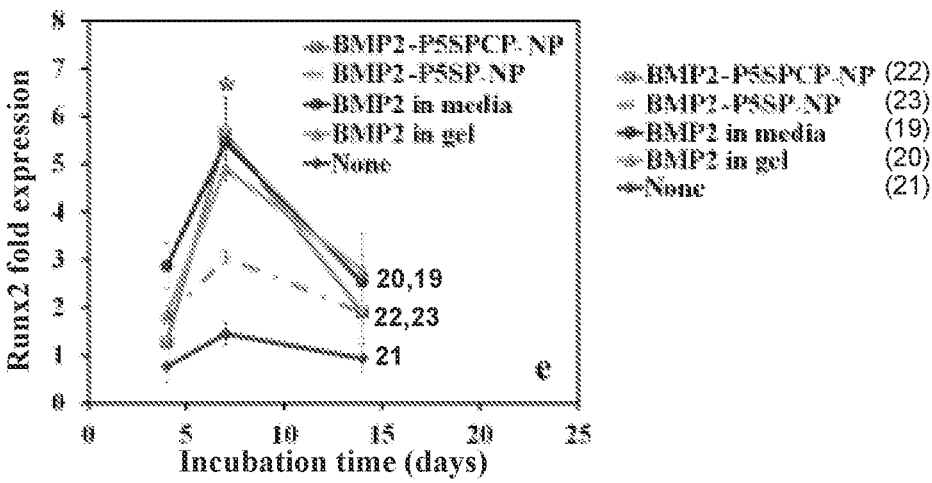
Figure 8F:
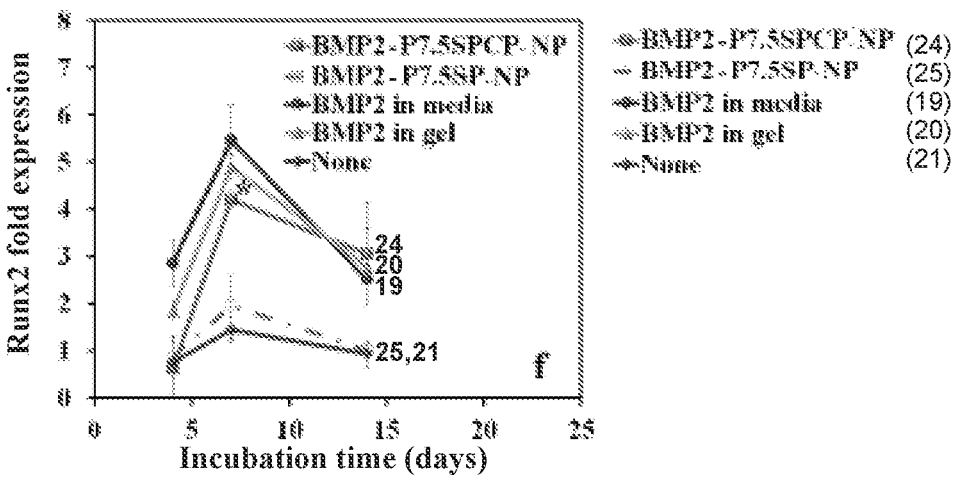
Figure 8G:
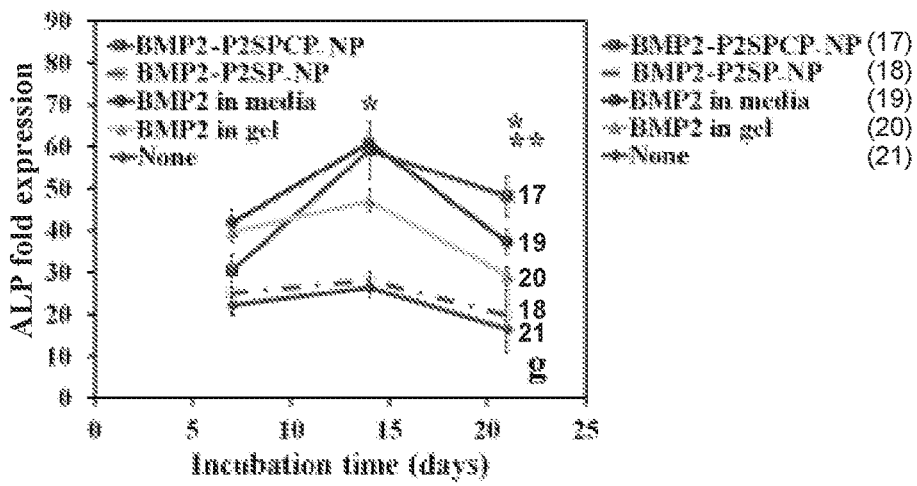
Figure 8H:
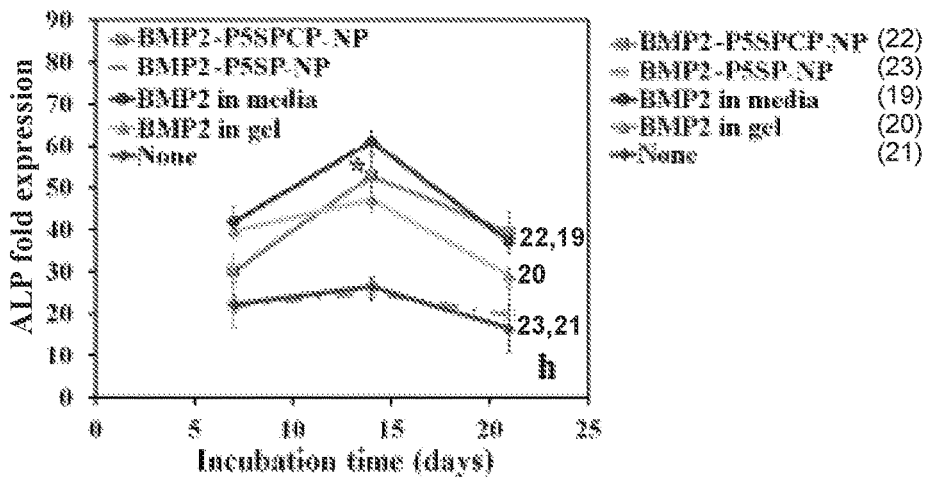
Figure 8I:
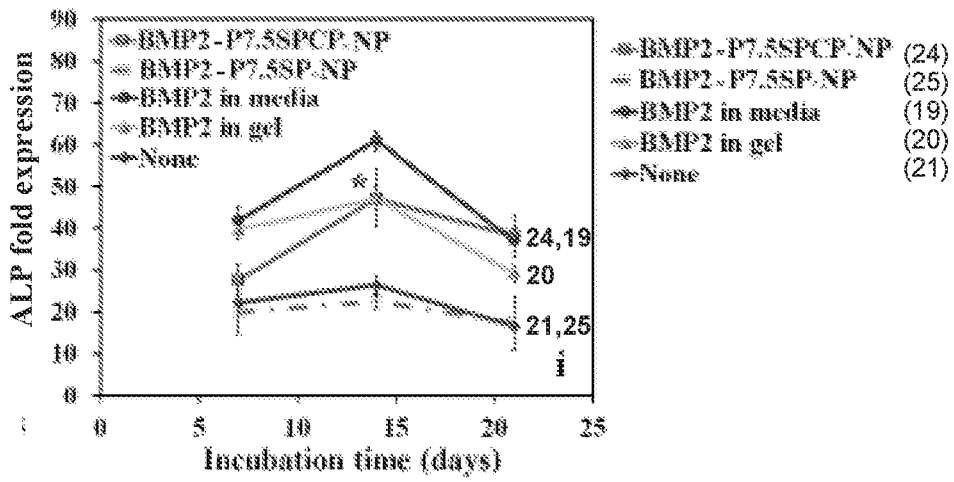

Osteogenic Activity of BMP2 Released from PxSPCP NPs: BMP2-PxSPCP NPs (PEG MW of 2 kDa, 5 kDa, and 7.5 kDa) and hMSCs were co-encapsulated in LPELA hydrogel, incubated in osteogenic medium without DEX, and the extent of osteogenesis was measured with incubation time. The DNA contents of hMSCs with incubation time for BMP2-PxSPCP NPs with PEG MW of 2 kDa, 5 kDa, and 7.5 kDa are shown in FIGS. 8A-8C, respectively; mRNA expressions of RUNX2 are shown in FIGS. 8D-8F; and ALP mRNA expressions are shown in FIGS. 8G-8I. Experimental groups included BMP2-P2SPCP NPs (17), BMP2-P2SP NPs (18), BMP2-PSSPCP NPs (22), BMP2-PSSPCP NPs (23), BMP2-P7.5SPCP NPs (24), and BMP2-P7.5SP NPs (25) co-encapsulated with hMSCs in LPELA hydrogel. Control groups were hMSCs encapsulated in LPELA hydrogel and incubated in osteogenic medium supplemented with (19) or without (21) BMP2, and hMSCs co-encapsulated with BMP2 in the hydrogel and incubated in osteogenic medium without DEX (20). The DNA content of all groups decreased with incubation time. DNA content of those groups incubated in osteogenic medium without BMP2 or with BMP2-PxSP NPs decreased at a slower rate compared to those with BMP2 or BMP2-PxSPCP NPs, consistent with previous reports.

The expression of RUNX2 initially increased from day 4 to 7 for all experimental groups, peaked on day 7, followed by a decrease from day 7 to 14 for all BMP2-PxSPCP NPs (FIGS. 8D-8F). Osteogenic activity of the experimental groups was measured by peak RUNX2 expression of the encapsulated hMSCs. Osteogenic activity of the group with BMP2 added to the medium was higher than the group with BMP2 co-encapsulated with hMSCs in the hydrogel, which was attributed to denaturation of a small but significant fraction of the encapsulated BMP2 during hydrogel formation. Osteogenic activity of BMP2-PxSP NP groups (dash lines: 18, 23, and 25, respectively, in FIGS. 8D-8F) was similar to that of no BMP2 group (21 in FIGS. 8D-8F), demonstrating that BMP2 grafted to non-cleavable NPs had negligible osteogenic activity. The BMP2-PxSPCP NP groups showed significantly higher osteogenic activity compared to non-cleavable BMP2-PxSP NPs, thus confirming that a significant fraction of BMP2 grafted to BMP2-PxSPCP NPs was cleaved by plasmin secreted by the encapsulated cells. Further, osteogenic activity of BMP2-P2SPCP-NP and BMP2-P5SPCP-NP groups (17 in FIG. 8D and 22 in FIG. 8E) were similar to that of free BMP2 added to the culture medium, whereas that of BM2-P7.5SPCP-NP group (24 in FIG. 8F) was lower. This result was attributed to higher availability of the plasmin-cleavable peptide in P2SPCP and PSSPCP NPs for enzymatic cleavage. The peak RUNX2 expression of hMSCs for BMP2-P2SPCP-NP and BMP2-PSSPCP-NP groups was 5.7, which was significantly higher than BMP2-P7.5SPCP-NP at 4.2.

FIGS. 8A-8I display DNA content (8A-8C) and mRNA expression of osteogenic markers RUNX2 (8D-8F) and ALP (8G-8I) with incubation time for hMSCs co-encapsulated with BMP2-PxSPCP NPs (PEG MW of 2 kDa, 5 kDa, or 7.5 kDa) in LPELA hydrogel and incubated in osteogenic medium (without DEX). FIGS. 8A, 8D and 8G are for DNA content and expressions of RUNX2 and ALP for BMP2-P2SPCP NPs (solid brown), respectively; FIGS. 8B, 8E and 8H are for BMP2-PSSPCP NPs (solid gray); and FIGS. 8C, 8F and 8I are for BMP7.5SPCP NPs (solid blue). Groups included BMP2-P2SPCP NPs (17), BMP2-P2SP NPs (18), BMP2-P5SPCP NPs (22), BMP2-PSSPCP NPs (23), BMP2-P7.5SPCP NPs (24), and BMP2-P7.5SP NPs (25) co-encapsulated with hMSCs in LPELA hydrogel. Control groups were hMSCs encapsulated in LPELA hydrogel and incubated in osteogenic medium supplemented with BMP2 (19) or without BMP2 (21), and hMSCs co-encapsulated with free BMP2 in the hydrogel (green) and incubated in osteogenic medium without BMP2 or DEX (20). Error bars correspond to means ±1 SD for n=3.

ALP mRNA expression of the encapsulated hMSCs peaked on day 14 for all experimental groups (FIGS. 8G-8I). Similar to RUNX2 expressions, the peak ALP expression of the group with BMP2 added to the medium was higher than the group with BMP2 co-encapsulated with hMSCs in the hydrogel; peak ALP expression of BMP2-PxSP NP groups (dash lines: 18, 23, and 25, respectively, in FIGS. 8G-8I) was similar to that of the no BMP2 group (21 in FIGS. 8D-8F); and peak ALP expression of BMP2-PxSPCP NP groups was significantly higher than the non-cleavable BMP2-PxSP NPs. The BMP2-P2SPCP-NP group (17 in FIG. 8G) had the highest peak ALP expression followed by BMP2-P5SPCP (22 in FIG. 8H), with BMP2-P7.5SPCP (24 in FIG. 8I) as the lowest. The peak ALP expression of hMSCs for BMP2-P2SPCP-NP, BMP2-P5SPCP-NP and BMP2-P7.5SPCP-NP groups was 60, 52 and 48, respectively. As P2SPCP NPs had the most stable size distribution (FIGS. 6A-6B), negligible loss of secondary structure of the grafted protein (FIG. 6C), and highest osteogenic activity of the grafted BMP2 (FIGS. 8A-8I), these NPs were selected for co-culture experiments with hMSCs and ECFCs in the patterned hydrogels.

Osteogenic and Vasculogenic Differentiation of hMSCs and ECFCs in Patterned Hydrogels with Plasmin-Cleavable BMP2-P2SPCP NPs: The effect of on-demand release of BMP2 from plasmin-cleavable NPs on osteogenesis and vasculogenesis was investigated in patterned hydrogels consisting of GelMA microchannels encapsulating hMSCs+ECFCs/VEGF-NGs in LPELA matrix encapsulating hMSCs/BMP2-P2SPCP-NPs. The results are shown in FIGS. 9A-9F, FIG. 10, FIGS. 11A-11G, and FIG. 12. All experimental groups were cellular. The groups included patterned constructs with BMP2-P2SPCP-NP in LPELA matrix and VEGF-NG in GelMA channels (BMP2-P2SPCP-NP/VEGF-NG, 27); unpatterned constructs with BMP2-P2SPCP-NP+VEGF-NG in a mixture of LPELA+GelMA with a composition identical to the patterned matrix (BMP2-P2SPCP-NP+VEGF-NG UnP, 26); patterned constructs with BMP2-P2SPCP-NP in LPELA and GelMA channels without VEGF (BMP2-P2SPCP-NP, 28); patterned constructs with LPELA without BMP2 and VEGF in GelMA channels (VEGF-NG, 32, see FIGS. 11A-F); patterned constructs with BMP2 in LPELA and VEGF in GelMA (BMP2/VEGF, 29); patterned constructs without BMP2 or VEGF (None, 30); and unpatterned constructs based on a mixture of LPELA+GelMA with a composition identical to the patterned matrix without BMP2 or VEGF (None UnP, 31).

The DNA content, calcium content, ALP activity, mRNA expression of osteogenic makers RUNX2, ALP, and Col I of the patterned cellular constructs are shown in FIGS. 9A-F. FIGS. 9A-F display DNA content (A), mRNA expression of osteogenic markers RUNX2 (B), ALP (C), Col I (D) and calcium content (E), and ALP activity (F) with incubation time for hMSCs and ECFCs encapsulated in the patterned constructs. Groups included patterned constructs with BMP2-P2SPCP-NP/VEGF-NG (27), patterned with BMP2/VEGF (29), unpatterned with BMP2-P2SPCP-NP/VEGF-NG (26), patterned with NP-P2SPCP-NP (28), patterned without BMP2/VEGF (30), and unpatterned without BMP2/VEGF (31). An asterisk represents a statistically significant difference between the test and "None" groups for the same time point. Two asterisks represent a significant difference between the test group and the patterned BMP2/VEGF group. Error bars correspond to means ±1 SD for n=3.

Figure 9A:
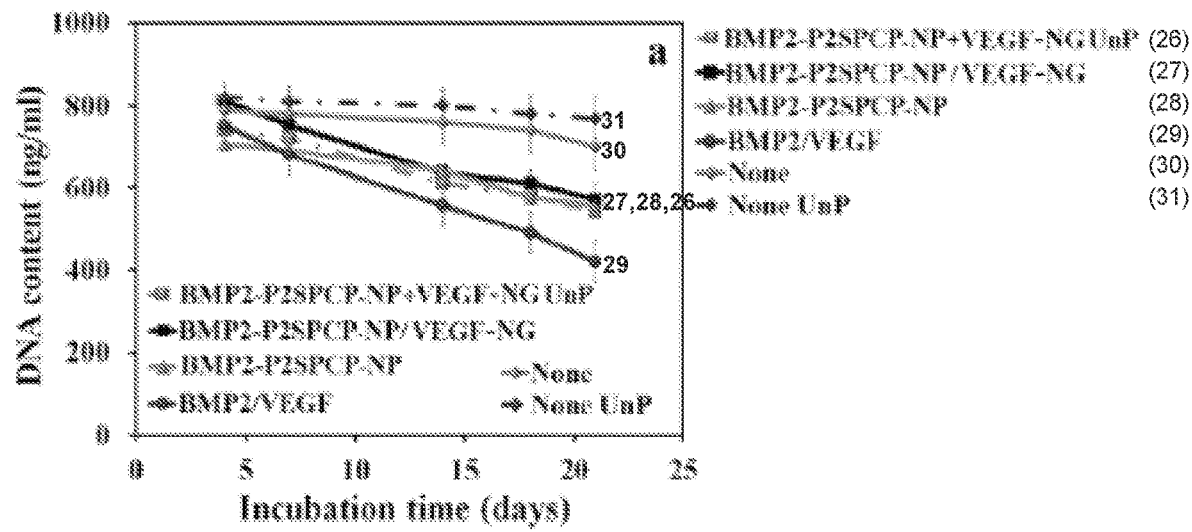
FIGS. 9A-9F illustrate graphs displaying aspects of exemplary embodiments in accordance with the disclosure.
Figure 9B:
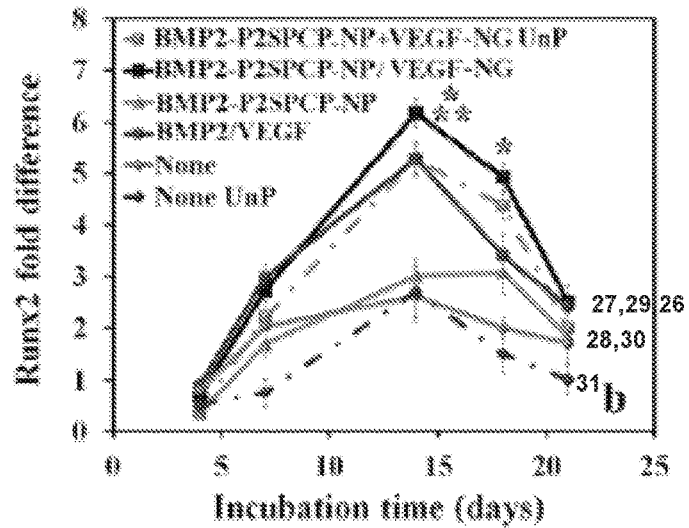
Figure 9C:
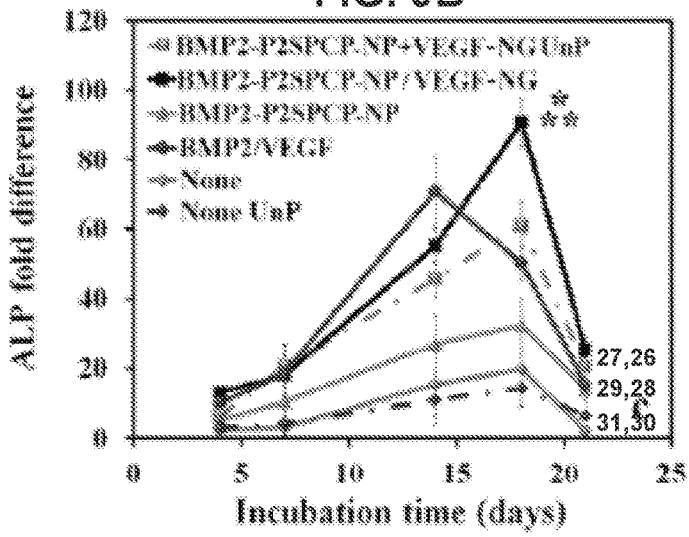
Figure 9D:
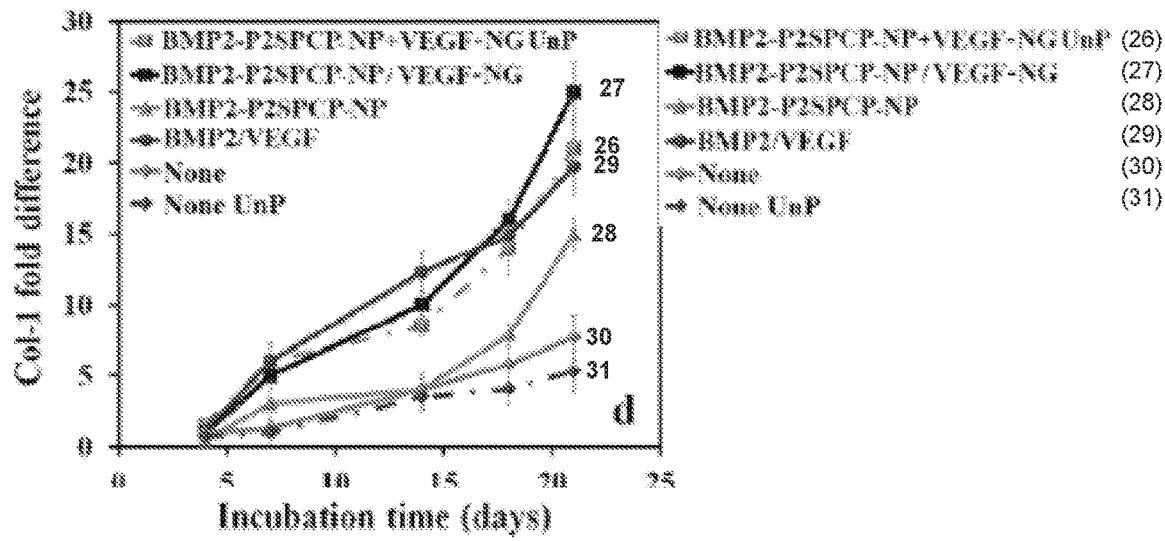
Figure 9E:
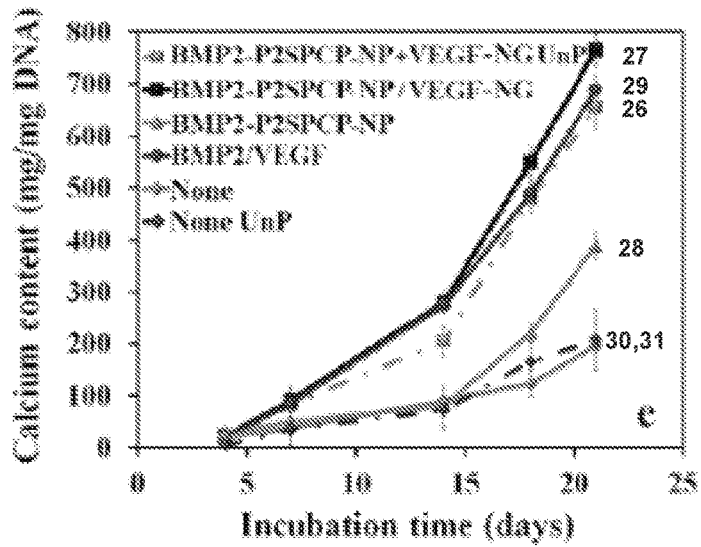
Figure 9F:
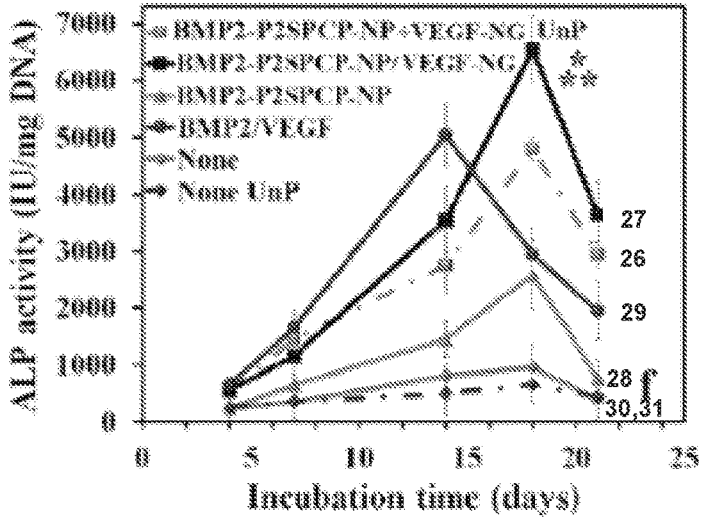
Figure 10:
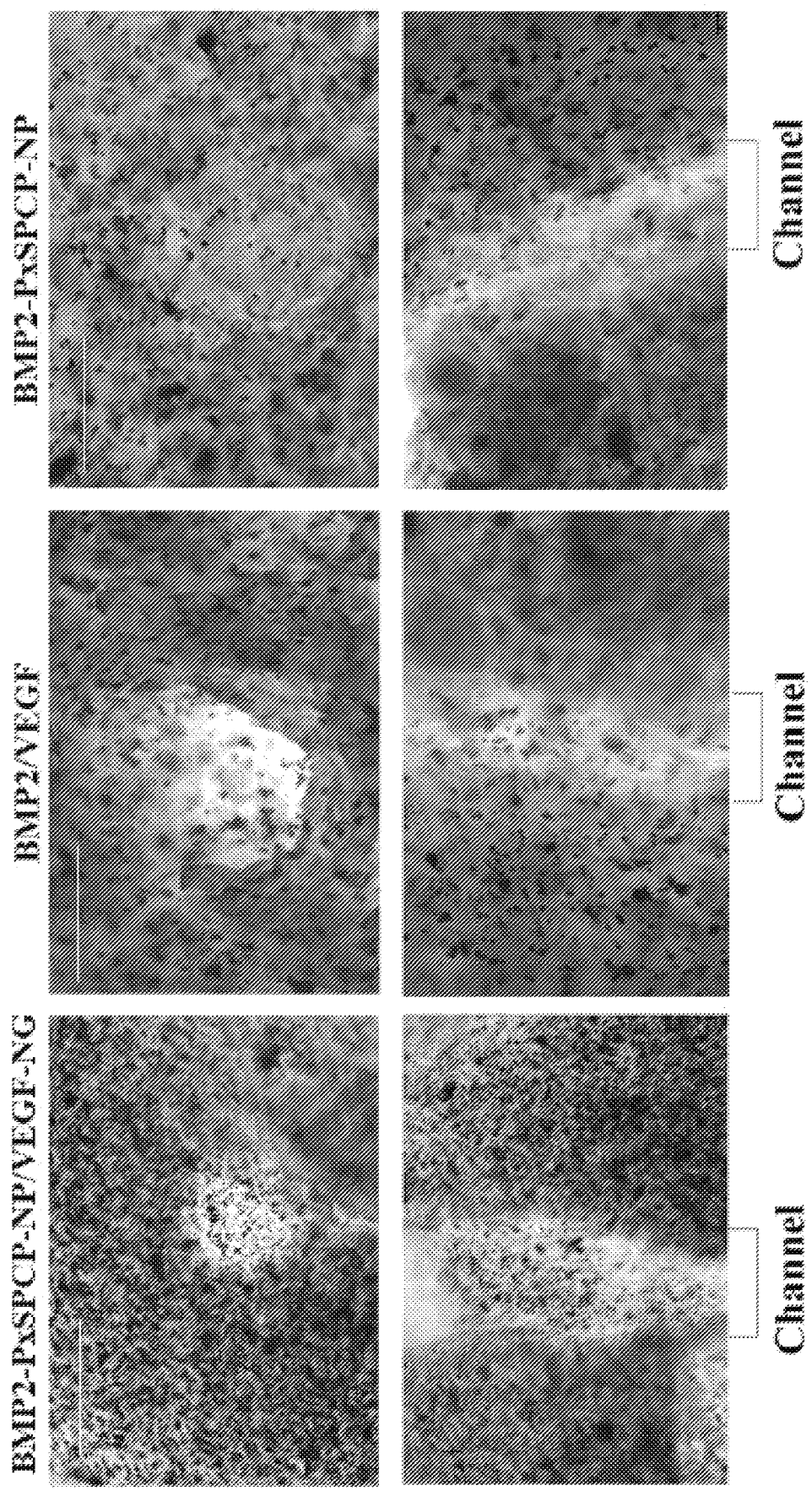
FIG. 10 illustrates stained images taken of channels of a cellular construct under the conditions shown. The top images provide a view of a cross-section of the channel. The bottom images provide a view of the length of the channel.
Figure 11A:
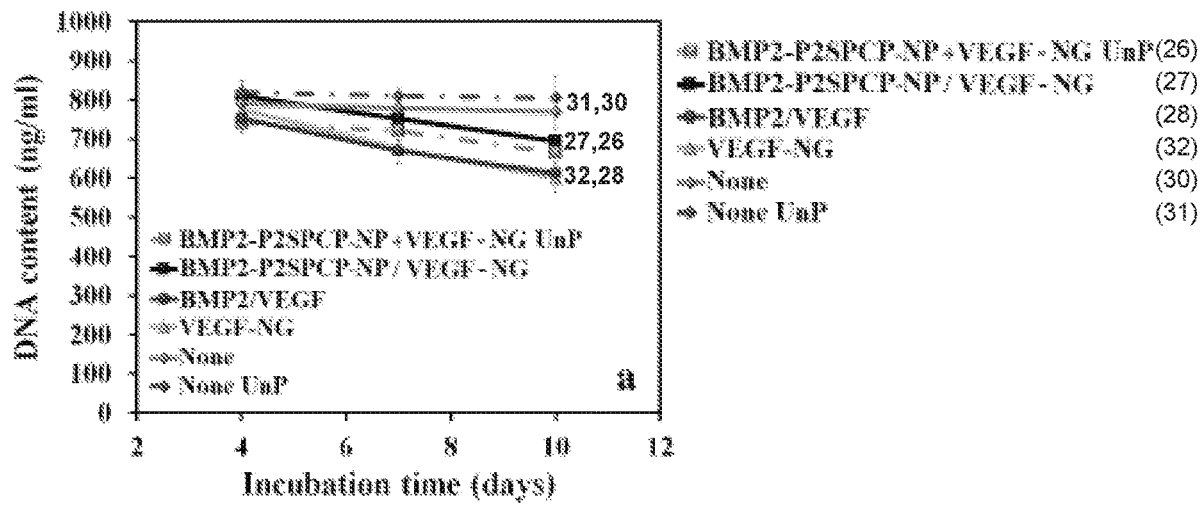
FIGS. 11A-11F illustrate graphs displaying aspects of exemplary embodiments in accordance with the disclosure.
Figure 11B:
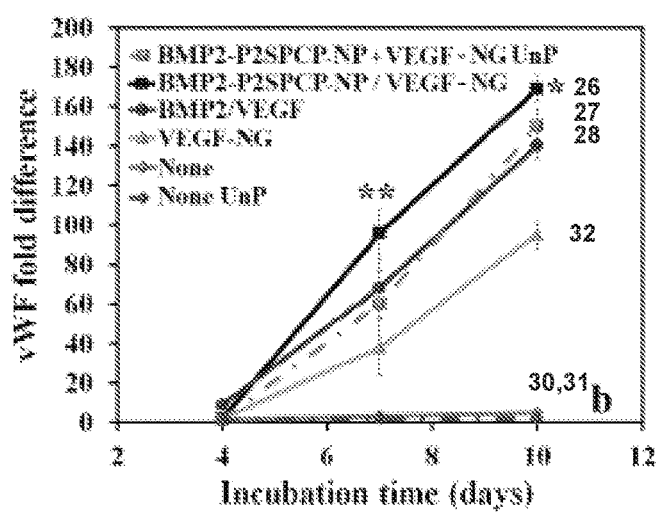
Figure 11C:
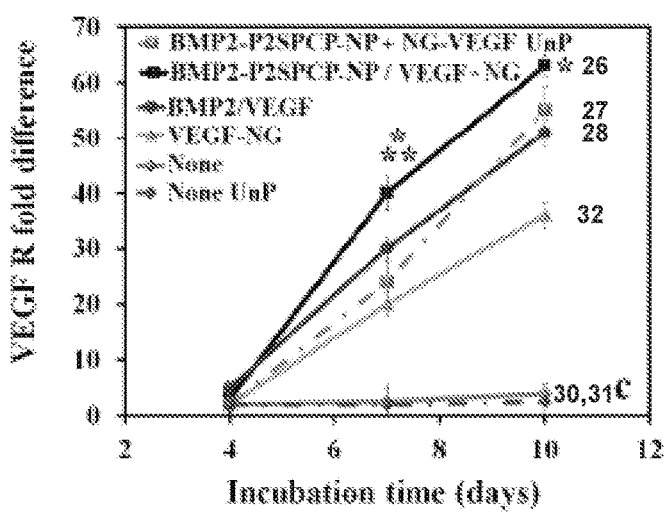
Figure 11D:
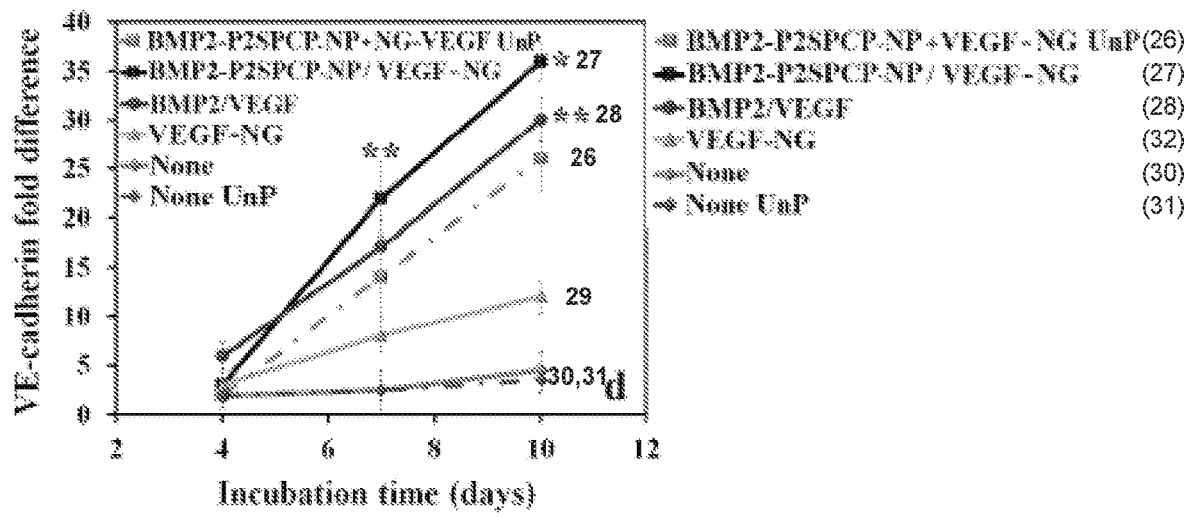
Figure 11E:
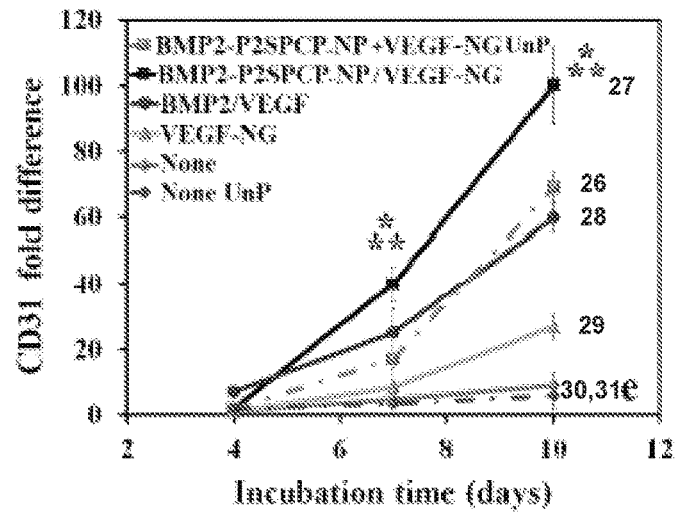
Figure 11F:
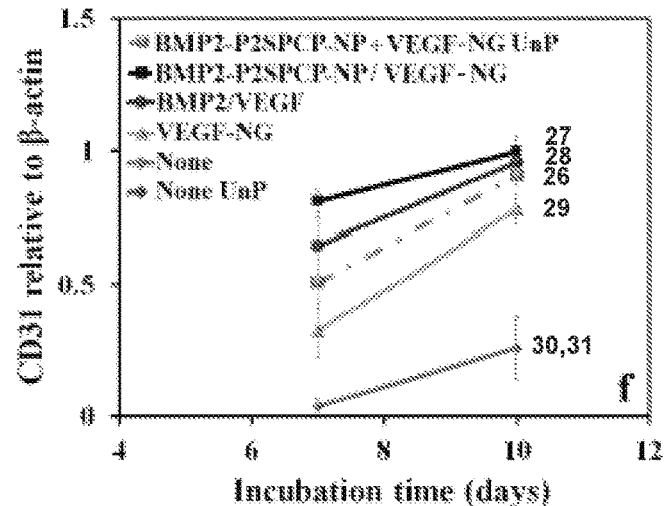
Figure 11G:
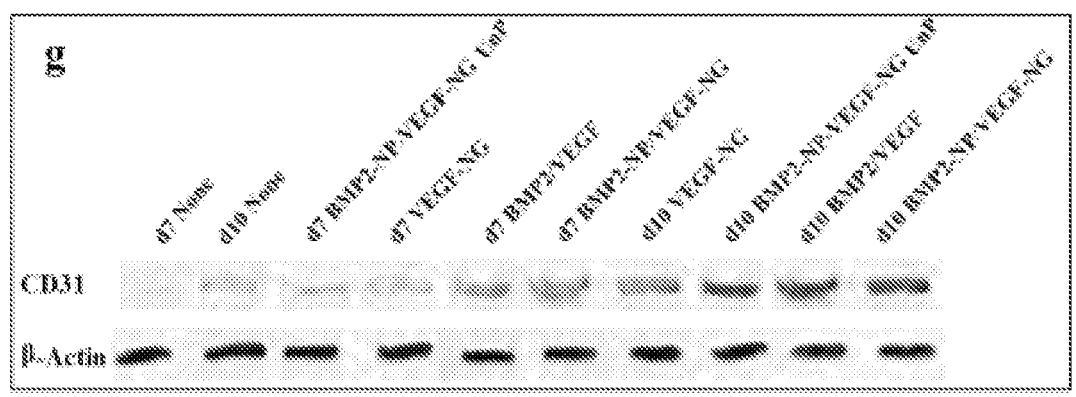
FIG. 11G illustrates a western blot stained for a protein (CD31 or β-Actin) under the condition shown in accordance with embodiments of the disclosure.

The DNA content of all BMP2 or BMP2/VEGF groups (FIG. 9A) decreased with incubation time, consistent with previous reports. For all groups, RUNX2 expression (FIG. 9B) of the encapsulated cells peaked on day 14, whereas Col I expression (FIG. 9D) and calcium content (FIG. 9E) steadily increased with incubation time. For the NP groups, ALP activity peaked on day 18 (FIGS. 9C and 9F), whereas it peaked on day 14 for the free BMP2/VEGF group. The groups with BMP2 and VEGF (with or without grafting to NPs/NGs) had the highest peak expression of osteogenic markers RUNX2 and ALP, as well as the highest Col I expression and calcium content on day 21. Among the groups with BMP2 and VEGF, the patterned BMP2-P2SPCP-NP/VEGF-NG group had the highest expression of osteogenic markers followed by the patterned BMP2/VEGF, unpatterned BMP2-P2SPCP-NP+VEGF-NG, and patterned BMP2-P2SPCP-NP groups. For example, the Col I-fold expressions of patterned BMP2-P2SPCP-NP/VEGF-NG, patterned BMP2/VEGF, unpatterned BMP2-P2SPCP-NP+ VEGF-NG, and patterned BMP2-P2SPCP-NP groups were 25, 20, 22, and 15, respectively (FIG. 9D); the calcium contents were 770, 695, 665, and 390 mg/mg DNA (FIG. 9E); and ALP activities were 6600, 5000, 4850, and 2550 IU/mg DNA (FIG. 9F). Interestingly, the calcium content, ALP activity, and expression of osteogenic markers for patterned BMP2-P2SPCP-NP group was significantly less than those of BMP2-P2SPCP-NP/VEGF-NG, BMP2/VEGF and unpatterned BMP2-P2SPCP-NP+VEGF-NG groups. This finding can be attributed to the lack of paracrine signaling between hMSCs and ECFCs in the absence of VEGF-NGs. The images for Alizarin red staining of the patterned BMP2-P2SPCP-NP/VEGF-NG, BMP2/VEGF and BMP2-P2SPC-NP groups are shown in FIG. 10. FIG. 10 displays grayscale images of Alizarin red-stained photographs around one of the channels of the cellular constructs for patterned BMP2-P2SPCP-NP/VEGF-NG (left), patterned BMP2/VEGF (center), and patterned BMP2-P2SPCP-NP (right) groups after 21 days of incubation. The top and bottom rows show the stained images in cross-section and along the length of the channel, respectively. The images show robust mineralization and nodule formation for these groups with the patterned BMP2-P2SPCP-NP/VEGF-NG group showing the most intense staining.

The DNA content, mRNA expression of vasculogenic markers vWF, VEGFR and VE-cadherin, and protein expression of CD31 vasculogenic marker of the patterned constructs are shown in FIGS. 11A-11G. FIGS. 11A-11G display DNA content (A), mRNA expression of vasculogenic markers vWF (B), VEGFR (C), VE-cadherin (D), CD31 (E), and CD31 protein expression (F), along with representative western blot bands (G) with incubation time for hMSCs and ECFCs encapsulated in the patterned constructs. Groups included patterned constructs with BMP2-P2SPCP-NP/VEGF-NG (27), patterned with BMP2/VEGF (29), unpatterned with BMP2-P2SPCP-NP/VEGF-NG (28), patterned with VEGF-NG (32), patterned without BMP2/VEGF (30), and unpatterned without BMP2/VEGF (31). An asterisk represents a statistically significant difference between the test and "None" groups for the same time point. Two asterisks represent a significant difference between the test group and the patterned VEGF/BMP2 group. Error bars correspond to means ±1 SD for n=3.

Figure 12:
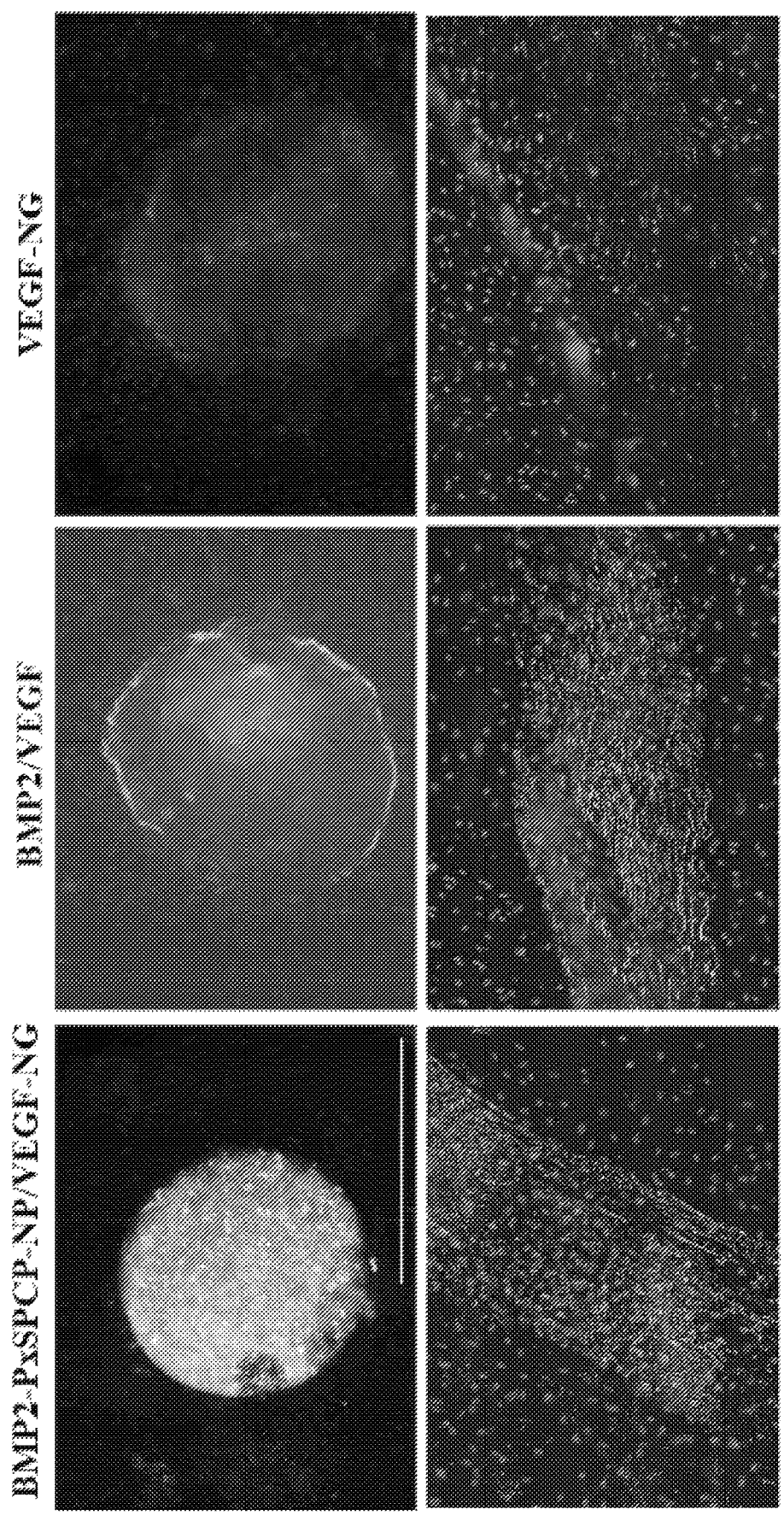
FIG. 12 illustrates stained images around an example channel of the cellular construct. The top images provide a view of a cross-section of the channel. The bottom images provide a view of the length of the channel.

DNA content of the groups with BMP2/VEGF or VEGF only decreased with incubation time with differentiation of the encapsulated hMSCs and ECFCs. The expression of vasculogenic markers for the groups with BMP2/VEGF or VEGF only increased with incubation time, whereas the expression for those groups without BMP2 or VEGF did not change significantly. After 10 days of incubation, the patterned BMP2-P2SPCP-NP/VEGF-NG group (27 in FIGS. 11A-11G) had the highest mRNA expression of vasculogenic markers vWF, VEGFR, VE-cadherin, and CD31, as well as the highest CD31 protein expression followed by the patterned BMP2/VEGF (28 in FIGS. 11A-11G), unpatterned BMP2-P2SPCP-NP+VEGF-NG (26 in FIGS. 11A-11G), and patterned VEGF-NG (32 in FIGS. 11A-11G) groups. For example, the normalized CD31 mRNA expressions (FIG. 11E) of the patterned BMP2-P2SPCP-NP/VEGF-NG, patterned BMP2/VEGF, unpatterned BMP2-P2SPCP-NP+ VEGF-NG, and patterned VEGF-NG groups were 100, 68, 60, and 28, respectively, and the normalized CD31 protein expressions of those groups were 1.0, 0.96, 0.9, and 0.75. Similar to the osteogenic markers in FIGS. 9A-9F, the expression of vasculogenic markers for the patterned VEGF-NG group was significantly less than the patterned BMP2-P2SPCP-NP/VEGF-NG, patterned BMP2/VEG, and unpatterned BMP2-P2SPCP-NP+VEGF-NG groups. The fluorescent images for CD31 immunostaining of the patterned BMP2-P2SPCP-NP/VEGF-NG, BMP2/VEGF, and the VEGF-NG groups are shown in FIG. 12. FIG. 12 displays immunofluorescent images of CD31 protein (white) around one of the channels of the cellular constructs for patterned BMP2-P2SPCP-NP/VEGF-NG (left), patterned BMP2/VEGF (center), and patterned BMP2-P2SPCP-NP (right) groups after 21 days of incubation. The top and bottom rows show the stained images in cross-section and along the length of the channel, respectively. The cell nuclei are counter-stained with DAPI (gray). The scale bar is 500 μm. The images show robust vascularization for the patterned BMP2-P2SPCP-NP/VEGF-NG, as well as for the BMP2/VEGF groups.

The invention claimed is:

1. A method for forming a hybrid multifunctional macromer, the method comprising:
synthesizing a backbone amino acid sequence by linking 4-26 amino acids, the backbone amino acid sequence comprising a cleavage site cleavable by an enzyme, wherein the cleavage site comprises a first amino acid sequence comprising KFYK (lysine-phenylalanine-tyrosine-lysine; SEQ ID NO: 2);
synthesizing an assembly peptide by linking an assembly site to an amino acid side chain included in the backbone amino acid sequence; and
attaching a solubility region to the assembly peptide, wherein the assembly site comprises a second amino acid sequence, wherein the second amino acid sequence comprises between 2-8 amino acid residues, and wherein the solubility region comprises a water-soluble polymer.

2. The method of claim 1, wherein synthesizing the backbone amino acid sequence comprises chemically attaching the 4-26 amino acids.

3. The method of claim 1, wherein the second amino acid sequence comprises at least one phenylalanine.

4. The method of claim 1, wherein the enzyme comprises plasmin.

5. The method of claim 1, wherein the solubility region comprises polyethylene glycol having a molecular weight between about 1.2 kDa to about 9 kDa.

6. The method of claim 1, wherein the cleavage site comprises a plasmin cleavage site.

7. The method of claim 6, wherein the cleavage site comprises SEQ ID NO: 1.

8. The method of claim 6, wherein the cleavage site comprises an MMP cleavage site.

9. The method of claim 1, further comprising attaching a linker.

10. The method of claim 1, further comprising attaching an endcap.

11. The method of claim 9, wherein the linker comprises a succinimide group.

12. The method of claim 10, wherein the endcap comprises a protein.

13. The method of claim 1, wherein the assembly site is not linked to a peptide backbone included in the hybrid multifunctional macromer.

14. The method of claim 1, further comprising attaching at least one spacer.

15. The method of claim 14, wherein the spacer comprises glycine.

16. The method of claim 1, wherein the assembly site comprises an N-acetylated residue.

17. The method of claim 1, wherein the 2-8 amino acid residues are sequentially-linked.

18. The method of claim 17, wherein the 2-8 amino acid residues are sequentially-linked phenylalanine residues.

* * * * *

SEQUENCE LISTING

```
Sequence total quantity: 17
SEQ ID NO: 1          moltype = AA  length = 12
FEATURE               Location/Qualifiers
REGION                1..12
                      note = Description of Artificial Sequence: Synthetic peptide
source                1..12
                      mol_type = protein
                      organism = synthetic construct
SEQUENCE: 1
GGKFYKGGKG GC                                                             12

SEQ ID NO: 2          moltype = AA  length = 4
FEATURE               Location/Qualifiers
REGION                1..4
```

```
                    note = Description of Artificial Sequence: Synthetic peptide
source              1..4
                    mol_type = protein
                    organism = synthetic construct
SEQUENCE: 2
KFYK                                                                      4

SEQ ID NO: 3        moltype = AA   length = 7
FEATURE             Location/Qualifiers
REGION              1..7
                    note = Description of Artificial Sequence: Synthetic peptide
source              1..7
                    mol_type = protein
                    organism = synthetic construct
SEQUENCE: 3
QPQGLAK                                                                   7

SEQ ID NO: 4        moltype = AA   length = 4
FEATURE             Location/Qualifiers
REGION              1..4
                    note = Description of Artificial Sequence: Synthetic peptide
source              1..4
                    mol_type = protein
                    organism = synthetic construct
SEQUENCE: 4
FFFF                                                                      4

SEQ ID NO: 5        moltype = AA   length = 8
FEATURE             Location/Qualifiers
REGION              1..8
                    note = Description of Artificial Sequence: Synthetic peptide
source              1..8
                    mol_type = protein
                    organism = synthetic construct
SEQUENCE: 5
FFFFFFFF                                                                  8

SEQ ID NO: 6        moltype = AA   length = 8
FEATURE             Location/Qualifiers
REGION              1..8
                    note = Description of Artificial Sequence: Synthetic peptide
source              1..8
                    mol_type = protein
                    organism = synthetic construct
SEQUENCE: 6
VVVVVVKK                                                                  8

SEQ ID NO: 7        moltype = AA   length = 4
FEATURE             Location/Qualifiers
REGION              1..4
                    note = Description of Artificial Sequence: Synthetic peptide
source              1..4
                    mol_type = protein
                    organism = synthetic construct
SEQUENCE: 7
GFFF                                                                      4

SEQ ID NO: 8        moltype = AA   length = 4
FEATURE             Location/Qualifiers
REGION              1..4
                    note = Description of Artificial Sequence: Synthetic peptide
source              1..4
                    mol_type = protein
                    organism = synthetic construct
SEQUENCE: 8
GRGD                                                                      4

SEQ ID NO: 9        moltype = AA   length = 4
FEATURE             Location/Qualifiers
REGION              1..4
                    note = Description of Artificial Sequence: Synthetic peptide
SITE                4
                    note = MOD_RES -
                     Lys(alpha-fluorenylmethyloxycarbonyl-epsilon-4-methyltrityl
                    )
source              1..4
                    mol_type = protein
                    organism = synthetic construct
SEQUENCE: 9
```

```
CGGK                                                                              4

SEQ ID NO: 10           moltype = AA   length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 10
GFFF                                                                              4

SEQ ID NO: 11           moltype = AA   length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 11
CGGK                                                                              4

SEQ ID NO: 12           moltype = AA   length = 4
FEATURE                 Location/Qualifiers
REGION                  1..4
                        note = Description of Artificial Sequence: Synthetic peptide
SITE                    4
                        note = MOD_RES - Lys, wherein the side chain of Lys is
                         connected to the sequence
                         GFFF-acetyl-alpha-fluorenylmethyloxycarbonyl
source                  1..4
                        mol_type = protein
                        organism = synthetic construct
SEQUENCE: 12
CGGK                                                                              4

SEQ ID NO: 13           moltype = AA   length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 13
KFKT                                                                              4

SEQ ID NO: 14           moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 14
GGKFKTGG                                                                          8

SEQ ID NO: 15           moltype = AA   length = 12
FEATURE                 Location/Qualifiers
REGION                  1..12
                        note = Description of Artificial Sequence: Synthetic peptide
SITE                    4
                        note = MOD_RES - Lys, wherein the side chain of Lys is
                         connected to the sequence GFFF-acetyl
source                  1..12
                        mol_type = protein
                        organism = synthetic construct
SEQUENCE: 15
CGGKGGKFKT GG                                                                    12

SEQ ID NO: 16           moltype = AA   length = 7
FEATURE                 Location/Qualifiers
REGION                  1..7
                        note = Description of Artificial Sequence: Synthetic peptide
SITE                    4
                        note = MOD_RES - Lys, wherein the side chain of Lys is
                         connected to the sequence GFFF-acetyl
source                  1..7
                        mol_type = protein
                        organism = synthetic construct
```

```
SEQUENCE: 16
CGGKGGG                                                                         7

SEQ ID NO: 17          moltype = AA   length = 12
FEATURE                Location/Qualifiers
REGION                 1..12
                       note = Description of Artificial Sequence: Synthetic peptide
SITE                   9
                       note = MOD_RES - Lys, wherein the side chain of Lys is
                        connected to the sequence GFFF-acetyl
source                 1..12
                       mol_type = protein
                       organism = synthetic construct
SEQUENCE: 17
GGKFKTGGKG GC                                                                  12
```